(12) United States Patent
Tajima et al.

(10) Patent No.: US 8,413,489 B2
(45) Date of Patent: Apr. 9, 2013

(54) COLUMN TIP PROCESSING DEVICE AND COLUMN TIP PROCESSING METHOD

(75) Inventors: Hideji Tajima, Matsudo (JP); Osamu Segawa, Matsudo (JP); Masanari Tsujimura, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 0 days.

(21) Appl. No.: 12/665,430

(22) PCT Filed: Jun. 18, 2008

(86) PCT No.: PCT/JP2008/061146
§ 371 (c)(1),
(2), (4) Date: May 28, 2010

(87) PCT Pub. No.: WO2008/156113
PCT Pub. Date: Dec. 24, 2008

(65) Prior Publication Data
US 2010/0236324 A1    Sep. 23, 2010

(30) Foreign Application Priority Data
Jun. 19, 2007    (JP) .................................. 2007-161349

(51) Int. Cl.
*G01N 30/84*    (2006.01)
(52) U.S. Cl.
USPC ........................................................ 73/61.55
(58) Field of Classification Search ................. 73/61.57, 73/61.53, 61.55, 61.56
See application file for complete search history.

(56) References Cited

U.S. PATENT DOCUMENTS

| 4,753,775 | A | 6/1988 | Ebersole et al. |
| 5,895,631 | A | 4/1999 | Tajima |

(Continued)

FOREIGN PATENT DOCUMENTS

| EP | 0 198 413 A2 | 10/1986 |
| EP | 1835020 A1 | 9/2007 |

(Continued)

OTHER PUBLICATIONS

English Translation of International Search Report, Aug. 26, 2008, International Application No. PCT/JP2008/061146, Japanese Patent Office, 3 pages.

(Continued)

*Primary Examiner* — John Fitzgerald
(74) *Attorney, Agent, or Firm* — Haynes and Boone, LLP

(57) ABSTRACT

The present invention relates to a column tip processing device and a column tip processing method, and its objective is to enhance the contact between a packing and a fluid as a subject to be processed whereby accomplishing a highly efficient reaction as well as an accurate processing, which has a nozzle head having a single or multiple-channeled nozzle, a suction and discharge mechanism, one or more types of column tips in which a packing is enclosed, a stage provided with a fluid housing part group including a plurality of fluid housing parts in which various solutions are or can be housed, and moving means for moving the nozzle head relatively to the fluid housing part group, and also has a controlling part which controls the suction and discharge mechanism and the moving means with regard to quantities, pressure, flow rate, the number of cycles, time or position of the suction or discharge by the nozzle based on a structural requirement relating to the structure of the one or more types of column tips to be fitted to the nozzle and a processing requirement relating to the processing contents involving one or more types of subject fluids subjected to the suction or discharge of the column tips.

18 Claims, 15 Drawing Sheets

U.S. PATENT DOCUMENTS

2006/0133965 A1 6/2006 Tajima et al.
2010/0119416 A1* 5/2010 Tajima .......................... 422/102

FOREIGN PATENT DOCUMENTS

| JP | 08320274 A | 12/1996 |
| JP | 2004264044 A | 9/2004 |
| JP | 2006300589 A | 11/2006 |
| WO | WO88/09201 | 12/1988 |
| WO | WO2006/073170 A1 | 7/2006 |

OTHER PUBLICATIONS

English Translation of International Search Report on Patentability Chapter II, International Application No. PCT/JP2008/061146, Japanese Patent Office, 4pages.

* cited by examiner

COLUMN TIP PROCESSING DEVICE AND COLUMN TIP PROCESSING METHOD

CROSS REFERENCE

This application is a United States national phase application of co-pending international patent application number PCT/JP2008/061146, filed Jun. 18, 2008, which claims priority to Japanese patent application number 2007-161349, filed Jun. 19, 2007, the disclosures of which are incorporated herein by reference.

TECHNICAL FIELD

The invention relates to a column tip processing device and a column tip processing method.

BACKGROUND OF THE INVENTION

There is a liquid chromatograph using a principle of a liquid chromatography in which, to a cylindrical vessel having liquid inlet and outlet in the center of top and bottom disks referred to as a column, a particulate packing having 10 to several hundred microns in particle size referred to as a gel is plugged without allowing for any voids in the space sandwiched between the top and bottom disks intending to achieve a uniform and sufficient contact with the liquids, and then separation and purification of a substance, mainly of a protein, is conducted utilizing the interaction between a solute molecule and the gel upon allowing the liquid to run in a single direction using a pump and the like from any direction from the liquid inlet or outlet on the top or bottom. Currently, a gel for a liquid chromatography having a varying surface structure is marketed. One having an ion exchange group on the surface of a gel has a function as an ion exchange gel, and makes it possible to separate substances by an ion exchange chromatography utilizing an interaction between a solute molecule and an ionic charge.

For example, when using a liquid chromatography, the separation was based on the specificity or the nature of a protein due to a change in the concentration resulting from mixing of two or three solutions. In such a method, a packing is plugged in a column and equilibrated with a buffer with an affinity allowing an intended protein to be adsorbed, and then a sample protein solution dissolved in the same buffer is passed through the column to accomplish the adsorption onto the packing, to which then a buffer solution having a different concentration is applied from the top of the column using a pump and the like, whereby establishing a concentration gradient in the column. At the same time, the concentration gradient in the column is established, and the protein loses an affinity at a concentration corresponding to the affinity of the intended protein, whereby being released from the packing and eluted. Accordingly, when the concentration of the intended protein is unknown, a buffer system allowing for a concentration gradient over a wide range is employed, and after fractionation to a plurality of wells based on the concentration gradient, the absorbance is measured for example by a UV absorption detector to narrow the range, and thereafter a buffer system giving a narrow range of the concentration gradient is employed, whereby extracting the intended protein.

Nevertheless, such a conventional liquid chromatography requires expensive devices and buffer solutions as well as a trial-and-error-based and well-trained operation, and suffers from effects of the concentration and the flow rate of a developing buffer which is not negligible.

Moreover, in such a conventional column, since a liquid is allowed to run in a single direction in a particulate packing plugged in the column, the packing is plugged without allowing for any voids in the column to ensure a high probability of the contact of the packing with a liquid upon passing through it, resulting in the time period of the contact of the liquid with the packing which can be controlled only by the flow rate in the column. However, because of the control of the flow rate using a pump, a transporting medium for moving a liquid containing the intended substance as a processing subject will be required. Thus, a buffer solution will be required in a problematically large quantity which is several times, several ten times, several hundred times as that of the liquid, while the contact with the packing surface will not necessarily high.

In addition, in a conventional column, since a fluid runs only in a single direction and the packing is plugged without any void in a space sandwiched between the disks of the column, a certain fixed route through which the liquid runs in the packing tends to be established. Once such a fixed route is established, a part which can not participate in the reaction may problematically occur.

Also since the mobile phase flow rate or mobile phase concentration has more or less influence, a troublesome sophisticated control is required.

[Patent Document 1] EP No. 198413
[Patent Document 2] International Publication No. 88/09201
[Non-Patent Document 1] Liquid Chromatography Q&A, Itaru Matsushita, GIHODO SHUPPAN Co., Ltd., June, 2000
[Non-Patent Document 2] Practice in Liquid Chromatography, Akira Eto, SANKYO Co., Ltd., 1976

DISCLOSURE OF THE INVENTION

Problems to be Solved by the Invention

Accordingly, the first object of the invention is to provide a column tip processing device and a column tip processing method enabling a highly efficient reaction, thus a high separation performance which leads to a rapid processing, by enhancing the contact between a packing and a liquid as a subject to be processed. The second object of the invention is to provide a column tip processing device and a column tip processing method capable of being conducted with no need of a large quantity of transporting medium, thus being conducted with a small-scaled device. The third object of the invention is to provide a column tip processing device and a column tip processing method enabling an automatic processing of column tips continuously using a single device. The fourth object of the invention is to provide a column tip processing device and a column tip processing method enabling a highly accurate control of a liquid chromatography.

Means for Solving the Problems

A first aspect of the present invention is a column tip processing device including: a nozzle head having a single or multiple-channeled nozzle; a suction and discharge mechanism conducting suction or discharge of a gas via the nozzle; one or more types of column tips each having a tip-shaped vessel having a fitting opening to be fitted to the nozzle and a hollow end through which a fluid can flow in or out in response to the suction or discharge of the gas and a packing enclosed in the tip-shaped vessel; a stage provided with a fluid housing part group including a plurality of fluid housing parts into each of which the hollow end can be inserted and which house or can house various solutions; and moving means for moving the nozzle head relatively to the fluid housing part group; and also having a controlling part which controls the suction and discharge mechanism and the moving means with regard to quantities, pressure, flow rate, the number of cycles, time or position of suction or discharge by the nozzle based on a structural requirement relating to the structure of the one or more types of column tips to be fitted to the nozzle and a processing requirement relating to the processing contents involving one or more types of subject fluids subjected to the suction or discharge of the column tips.

As used herein, the term "packing" refers to an insoluble stationary phase used to adsorb or capture, or react with or bind to a biological substance contained in a subject fluid which is a subject for suction or discharge as a so-called mobile phase. Such a packing may include for example a certain particulate carrier on which surface a biological substance is placed or bound.

A "carrier" is an insoluble solid capable of adsorbing, reacting with, binding to, immobilizing or capturing a biological substance in a fluid, whose shape may include a plurality of solids such as a plurality of particles, powders, blocks and the like. A single particle may also be in the forms not only of spherical forms but also of columns, cylinders, irregular forms. The carrier may have a varying size, such as one allowing passage through the hollow end and being larger than the pore size of the filter discussed later here. The material for a carrier may for example be a gel, porous material, continuous pore-carrying material, hydrous material and the like made from fibers and resins such as rubbers, silicones, celluloses, nylons and the like, as well as metals such as non-magnetic particles, magnetic particles and the like. Such a carrier is provided with a chemical substance or a biological substance such as functional groups for the purpose of adsorption, reaction, binding, immobilization or capture of the biological substance. Also provided on the surface of the carrier may for example be antigens, antibodies, enzymes, substrates, receptors, affinity ligands such as His-tag, affinity tags and the like.

A "biological substance" may for example be a biopolymer or small molecule such as a genetic substance such as a nucleic acid, protein, saccharide, saccharide chain, peptide, and color. The biological substance may include a cell, virus, plasmid and the like. Such a biological substance may be employed as a detector which detects, captures, separates and extracts the binding of a biological substance as a receptor having an ability of binding to such a biological substance as a ligand. The receptor may for example be a genetic substance such as a nucleic acid, protein, saccharide and peptide as described above. A "filter" is a member for filtration or separation in a form of a thin film or thin sheet having a certain pore size, and, when provided in a manner to partition a fluid path, it prevents the passage of a substance larger than the pore size.

The phrase "absorb or capture the biological substance, or react with or bind to the biological substance" means that a reaction or binding is due to a covalent bond, chemical adsorption as well as physical adsorption or electrical interaction or capture in a pore of a certain size, or a specific reaction with a binding substance in which a certain chemical substance is adsorbed chemically or physically onto or immobilized on the carrier, and also due to other manners. The carrier may be formed also from a porous material, irregular surface material, fibrous material and the like, whereby enhancing the ability of reacting with or binding to various substances including biological substances. In order to immobilize complementary biological materials for the reaction with or binding to a biological substance, the carrier is allowed to express or generate a functional group. For this purpose, by hydrolyzing a peptide bond possessed by polyamide-based polymer"-derived silks, nylons (3-nylon, 6-nylon, 6,6-nylon, 6,10-nylon, 7-nylon, 12-nylon and the like), all aromatic polyamides such as polyparaphenylene terephthalamide (PPTA), heterocycle-containing aromatic polymers, a functional group used for immobilizing a biological substance is expressed or generated. Such a functional group capable of binding to a biological substance may for example be a carboxyl group (—COOH), an amino group (—NH2), or derivative thereof. The size of a pore suitable for immobilizing a biological substance may for example be several micrometers or less.

The phrase "to be fitted to a nozzle" includes a direct fitting to the nozzle and a fitting to a member to be fitted to the nozzle, such as tip, adapter and the like. The "tip" has a tube having a large diameter and a tube having a small diameter which is formed in fitting with the tube having a large diameter and which is formed in a size smaller than that of the tube having a large diameter, and the tube having a large diameter has a fitting opening to be fitted to the nozzle, and the tube having a small diameter has a hollow end through which a fluid can flow in or out in response to the suction or discharge of a gas.

A "tip-shaped vessel" is a vessel which has a fitting opening fitted or capable of being fitted to a member employed for the suction or discharge and in which a carrier can be housed. Although the tip-shaped vessel can have a thick tube and a narrow tube, there is no limitation to one having a typical tip shape such as a tube having a large diameter and a tube having a small diameter. In such a case, the narrow tube can have a hollow end and the thick tube can have a fitting opening on the upper side thereof. For example, the thick tube may have a form of a quadratic prism instead of a tube having a large diameter, and the narrow tube may be a pipe having a polygonal section instead of a tube having a small diameter. The thick tube may also be formed as a disk protruding in the direction of radius relative to the axial direction whereby reducing the length along with the axis. The packing is housed in a part corresponding to the thick part or a part corresponding to the transfer part between the thick tube and the narrow tube. In such a case, the stage provided on the part corresponding to the thick tube and another stage, at a distance from the stage, in the part corresponding to the transfer part may be utilized to partition the filters, and the packing may be sealed such that the packing is sandwiched between the filters. The capacity of the tip-shaped vessel is preferably one capable of handling a fluid in a quantity for example from several μ liters to several hundred μ liters. In the tip-shaped vessel, a reservoir tube which reserves a fluid introduced from the hollow end in addition to the part housing the packing as being enclosed may also be provided. Such a reservoir tube may be formed in a size larger than that of the narrow tube or than that of the thick tube. The narrow tube may be formed as being integrated with the thick tube or with the reservoir tube, or may be detachably formed therefrom. The thick tube itself, and the thick tube and the reservoir tube may be formed integrally or detachably.

The material for a tip-shaped vessel may be a light transmissible material for enabling an optical measurement. The material for the tip-shaped vessel may for example be a resin such as a polyethylene, polypropylene, polystyrene, acrylic material and the like, as well as a glass, metal, metallic compound and the like. The size may for example be one allowing several μ liters to several hundred μ liters to be housed in the narrow tube.

A "subject fluid" is a liquid serving as a subject to be suctioned to or discharged from the column tip, and may for example be a liquid containing an intended biological substance, such as a test sample containing a substance extracted and separated from a patient, study subject, animal and others, including a serum, whole blood and the like, and also includes a certain protein, or a series of buffers having a stepwise gradient of concentrations having a certain difference in concentration from each other which is housed in each fluid housing part described above, or various washing solutions employed for washing the column tips, eluents for eluting an intended substance, once adsorbed onto, captured by, reacted with or bound to the packing, from this packing.

The "structural requirement" is a requirement relating to the structure of a column tip required for setting with regard to suction or discharge, while the "processing requirement" is a requirement relating to the processing conducted by a column tip involving a subject fluid to be the suctioned and discharged. The structural requirement includes a plurality of items since a column tip having a relatively complicated structure is employed. The processing requirement also includes a plurality of items relating to the subject fluid.

The phrase "based on the structural requirement and the processing requirement, . . . quantities, pressure, flow rate, the number of cycles, time or position of the suction or discharge by the nozzle are controlled" is based on various factors serving as a resistance against the suction or discharge of a liquid such as filters, mesh plates present in the column tip as well as the presence of a plurality of stages provided in the tip-shaped vessel. Accordingly, for the purpose of conducting suction or discharge at a high accuracy, an appropriate suction or discharge control is performed, upon controlling suction or discharge utilizing a difference in the pressure of air which is an elastic fluid, while correcting the quantity, time and speed of suction or discharge based on the structural requirement and the processing requirement. For example, when the adsorption performance of the packing is lower than a required adsorption performance, then the time period for the contact is prolonged to promote the adsorption, resulting in a requirement of repetitive passages through the packing, which leads to increasing the number of suction and discharge cycles. In addition, in such a case a relatively slow suction serves to ensure the prevention of the detachment of an intended biological substance once adsorbed. In the case of a higher adsorption performance, it may be highly efficient to establish a suspending state with the packing by suctioning at a high speed.

Furthermore, it is also required to correct quantities, time, speed or pressure of the suction or discharge by taking the nature of the subject fluid as a subject of suction or discharge such as viscosity, temperature, quantity and processing contents into account based on the processing requirement. In addition, depending on the ratio between the packing and the column tip capacity included in the structural requirement, the quantity of the fluid capable of being suctioned is limited in order to prevent introduction of air. As used herein, the term "time" includes a time point and a timing. The term "position" includes the vertical position of the suction or discharge, in addition to the housing position for the subject fluid to be suctioned and discharged.

The suction and discharge is not necessarily limited to an actual suction and discharge of a liquid, and may be conducted based on the details of each step of such a processing.

For example, in a state where column tips are kept and when the packing activation maintaining fluid is housed in contact with the packing, then for the purpose of avoiding a phenomenon that the air layer in the opening becomes positive correspondingly to the nozzle volume upon nozzle fitting which prevents the fluid in a column tip to be splashed from the hollow end of the column tip which leads to a contamination, a suctioning action should be taken correspondingly to the nozzle volume upon fitting.

Also when transporting column tips by nozzle, a slight suction is conducted to avoid the leakage from the hollow end.

A second aspect of the invention is a column tip processing device, wherein the packing is enclosed in the tip-shaped vessel using at least one filter provided in a manner to partition the tip-shaped vessel, the structural requirement includes a plurality of items relating to the structure of the tip-shaped vessel, the structure of the filter or the morphology, type and nature of the packing enclosed, and the processing requirement includes a plurality of items relating to the processing contents including each housing position, type, nature or quantity of one or more types of the subject fluids subjected to the suction or discharge of the column tips.

The phrase "the structure of the member (fitted to the nozzle or the tip-shaped vessel" includes, for example, the positions of one or more nozzles having the tips as being fitted thereto, and the morphology and the size of a tip-shaped vessel. The term "the structure of a filter" includes the filter's pore size, pore density, thickness, area through which a fluid can pass, porosity, and the number of filters. The phrase "the morphology or nature of the packing enclosed" includes, for example when the packing is formed from a particulate carrier, the particle size, and the ratio of the volume of all particles to the capacity or available capacity of the column tip. The term "nature" includes the material employed for the packing, the degree of the adsorption, capture, reaction and binding performances of the packing for adsorbing, capturing, reacting with, binding to an intended biological substance. The phrase "nature of the subject fluid" includes the concentration of a biological substance contained in the subject fluid, the viscosity of the subject fluid and the like. When the rigidity of the filter is low and a mesh plate for supporting the filter is provided, then the pore size and the thickness of the mesh plate should also be taken into account.

Also by varying the ratio between the bead volume forming the packing and the tip-shaped vessel's capacity, and especially by selecting the packing volume which gives a ratio which allows the interstice instead of a densely enclosed state in the tip-shaped vessel whereby allowing suction or discharge to be conducted at a flow rate allowing a liquid turbulence to occur in the column tip, a sufficient contact between the packing and the subject fluid is ensured, whereby enabling a highly efficient processing. In addition, by taking the pore size or the number of pores per part area into account, an appropriate suction or discharge flow rate can be determined.

The phrase "processing contents" includes the types of one or more types of column tips to be employed, and a protocol showing how to process other tips to be employed in order to achieve the purpose of the processing for two or more s of the subject fluids. Those exemplified specifically include a case where a purification processing of a protein employing column tips is conducted, a case where a purification processing of a protein employing antibodies is conducted a purification of a protein recombinant, and a cases where major proteins in a serum are removed.

In a processing where an antibody is employed to purify a protein, a column tip enclosed with an affinity gel such as Protein A and Protein G as the packing is employed. After allowing a sample to be adsorbed onto the packing a glycine-HCl buffer solution was employed for elution, whereupon achieving the abovementioned purified antibody desalting or trace low molecular weight contaminant removal by means of a gel filtration chromatography.

In the case of purification of a recombinant protein, anti GST antibody or glutathione for purification of a GST fusion protein or histidine tag fusion protein, and a column tip enclosed with an affinity gel on which a nickel ion is immobilized are employed. After adsorbing a sample, elution is conducted using a salt solution at a high concentration or a solution of a reduced form of glutathione and an imidazole solution, and then the crude fusion protein solution is subjected to desalting or removal of low molecular weight contaminants using a gel filtration chromatography.

When major proteins in a serum are to be removed, a column tip enclosed with an affinity gel on which specific antibodies (several types) for the major proteins are immobilized is employed. The serum is bound to the specific antibodies by suction into and discharge from an equilibrated column tip, and after the final discharge the serum components free of the major proteins are recovered.

A third aspect of the invention is a column tip processing device wherein the controlling part has a designating part which designates the column tips and a processing using the column tips, a requirement generating part which generates a structural requirement relating to the designated column tips and a processing requirement relating to the designated processing, and an optimum parameter determining part which determines, based on the generated the structural requirement and processing requirement, an optimum parameter with which the suction and discharge mechanism and the moving means should be in accordance.

The designating part is used for example in such a manner that a user uses a mouse to click a switch or indication on a display to select each one of a plurality of column tips and a plurality of processings, or a user uses a keyboard to enter a number. Based on the column tip and the processing designated by the designating part, the structural requirement and the processing requirement were specified, and then based on the specified structural requirement and the processing requirement an optimum parameter is determined for example by means of arithmetic calculation.

A fourth aspect of the invention is a column tip processing device, wherein the optimum parameter determining part determines an optimum parameter relating to suction or discharge, based on the generated corresponding structural requirement and processing requirement for each of the column tips and processing contents, in order to reduce the difference in time between the suction or discharge operation starting time for the suction and discharge mechanism and the fluid movement starting time for column tips and also the offset of suction or discharge operation quantity and the suction or discharge quantity of the fluid for the column tip after achieving the operation quantity.

As used herein, the "difference in time" is due to the fact that the liquid is not coming into a column tip immediately after operating a suction and discharge mechanism, such as a cylinder. The term "offset" means a differential quantity remaining between the actual liquid suction or discharge quantity and the operational quantity of the suction and discharge mechanism even after a sufficient time period has elapsed after completion of the operation of the suction and discharge mechanism. Accordingly, the suction or discharge operation quantity is a desired suction or discharge quantity complemented with the offset fluid quantity. In conjunction with the suction or discharge flow rate, the difference in time can be reduced by suctioning the fluid slowly when the resistance of the fluid in the column tip is high. Furthermore, the suction or discharge flow rate is selected while taking the reactivity and the reaction time of the ligand in the packing in the column tip with the subject substance to be captured.

The optimum parameter determining part may be in such a manner that the optimum parameter is determined based on a reference table which assigns to each of said column tips and processing contents an optimum parameter which was obtained previously while taking the generated corresponding structural requirement and the processing requirement into account.

Such a reference table is provided for each of the designated column tips and processing contents, and based on the structural requirement and processing requirement obtained from the reference table another reference table indicating an optimum parameter is provided and stored in a memory. Thus, in the present invention, instead of obtaining preliminarily each optimum parameter of the suction or discharge as a functional value of a multivalent function of each structural requirement and processing requirement with regard to the structure of a certain column tip by means of a numerical calculation, an optimum suction or discharge parameter, when each structural requirement and processing requirement are prescribed preliminarily, is specified by means of experiments whereby deriving the optimum parameter for the requirements.

Being based on "the structural requirement and processing requirement" naturally includes being based on the nature of the packing encompassed in the structural requirement and the details of the reaction with a substance contained in the subject fluid encompassed in the processing requirement.

A fifth aspect of the invention is a column tip processing device, wherein the optimum parameter determining means determines, based on a standard structural requirement which sets predetermined one or two standard column tips and at least a part of the plurality of the items of the structural requirement corresponding to the standard processing contents at one or more standard values and a standard processing requirement which sets at least a part of the plurality of the items of the processing requirement at one or more standard values, an optimum parameter corresponding to structural requirements and processing requirements other than the standard structural requirements and the standard processing requirement.

For predetermined one or more types of standard column tips, the standard structural requirement and the standard processing requirement are measured or prescribed, and then based on the standard structural requirement and the standard processing requirement, a standard optimum parameter is obtained for example by an experiment. Based on this, the optimum parameter value is changed depending on the comparison whether it is higher or lower than the standard value for a certain column tip, or the optimum parameter is determined by calculation using an interpolation.

Here, as "one or more types of standard column tips", one or more types of different types of column tips are provided, and for each type a reference table is prepared, and for a certain column tip a column tip similar to that column tip is designated.

A sixth aspect of the invention is a column tip processing device, wherein the stage has a temperature raising and lowering vessel which raises or lowers the temperature in response to an external signal, at least one of the fluid housing part is housed in the temperature raising and lowering vessel, and the control of the temperature of the subject fluid is conducted on the moving means based on the processing requirement.

Here, the temperature control is conducted by moving the nozzle to the temperature raising and lowering vessel provided on the stage.

A seventh aspect of the invention is a column tip processing device, wherein on the stage one or more said column tips, one filter tip having a fitting opening to be fitted to a nozzle, or one dispensing tip, and a detaching part for detaching the column tip, filter tip or dispensing tip fitted to the nozzle are provided, and the controlling part conducts, on the suction and discharge mechanism and the moving means, the control of the fitting and detachment of the column tip, filter tip or dispensing tip based on the structural requirement and the processing requirement.

As used herein, "two or more types of column tips" may be in the cases where the packing is different, where the filter is different, where the shape of the tip-shaped vessel is different, and where even if the packing is the same the ratio to the column tip capacity is different. Those which can be exemplified are a column tip for affinity chromatography in which a salt concentration is used to allow a protein to be adsorbed and a column tip enclosed with an agarose gel for desalting. The "filter tip" is one in which a filter is provided in a tip-shaped vessel in such a manner that it serves as a partition between the fitting opening and the hollow end. The "dispensing tip" is a tip-shaped vessel which allows a magnetic field to be applied to the inside from the outside. When using a dispensing tip, it is required to provide the nozzle head with a magnetic force means capable of applying a magnetic field to the inside of the dispensing tip.

An eighth aspect of the invention is a column tip processing device, wherein at least a part of the fluid housing part group is provided with a piercable thin film covering the opening of the fluid housing part, the nozzle head is provided with a piercing pin capable of piercing the thin film, and the control of the thin film piercing is conducted on the moving means based on the processing requirement.

A ninth aspect of the invention is a column tip processing device, wherein the nozzle head is provided with a fall off preventing part which prevents the fall off from the nozzle by engaging with the tip-shaped vessel of the column tip fitted to the nozzle, and the control of the fall off prevention and a cancellation thereof by the fall off preventing part is conducted on the moving means based on the structural requirement and the processing requirement.

Here, since the fall off preventing part engages with the tip-shaped vessel of the column tip, it can be applied also to a dispensing tip enclosed with no packing or to a filter nozzle when using an identical tip-shaped vessel. Such a fall off prevention and a cancellation thereof by the fall off preventing part is accomplished by moving control by the moving means.

A tenth aspect of the invention is a column tip processing method having: based on a structural requirement of one or more types of column tips each having a tip-shaped vessel having a fitting opening conducting suction or discharge of a gas by a suction and discharge mechanism and a hollow end through which a fluid can flow in or out in response to the suction or discharge of the gas and a packing enclosed in the tip-shaped vessel, and a processing requirement relating to the processing contents involving one or more types of subject fluids subjected to the suction or discharge of the column tips, a fitting step for fitting a column tip to the nozzle at the fitting opening by moving the nozzle relatively between it and the housing parts of the column tip housed therein; a contacting step for inserting the hollow end into the fluid housing part by a relative movement between one or more fluid housing part housing the subject fluid and the nozzle whereby suctioning and discharging the subject fluid according to quantities, pressure, flow rate, the number of cycles, time or position of the suction or discharge by the nozzle determined based on the requirement, whereby bringing the packing into contact with the subject fluid; and a discharging step for discharging the subject fluid from the column tip into one or more the fluid housing parts.

When in the column tip, a liquid for maintaining the packing activation is enclosed in a breakable manner together with the packing in such a manner that each of the fitting opening and the hollow end is closed in a removable state by the upper lid and the lower cap, then the cap removing step is provided after the fitting step.

An eleventh aspect of the invention is a column tip processing method, wherein the packing is enclosed in the tip-shaped vessel using at least one filter provided in a manner to partition the tip-shaped vessel, the structural requirement includes a plurality of items relating to the structure of the member or the tip-shaped vessel fitted to the nozzle, the structure of the filter or the morphology, type and nature of the packing enclosed, and the processing requirement includes a plurality of items relating to the processing contents including each housing position, type, nature or quantity of one or more types of the subject fluids subjected to the suction or discharge of the column tips.

A twelfth aspect of the invention is a column tip processing method, further having a designating step for designating column tips to be fitted and processing contents to be processed, and a generating step for generating a structural requirement corresponding to the column tips designated and generating a processing requirement corresponding to the processing contents designated, wherein the contacting step has an optimum parameter determining step for determining an optimum parameter based on the generated structural requirement and processing requirement, and a contact executing step for moving the nozzle while executing suction or discharge.

A thirteenth aspect of the invention is a column tip processing method, wherein the optimum parameter determining step determines suction or discharge parameters, based on the generated corresponding structural requirement and processing requirement for each of the column tips and processing contents, while considering the difference in time between the suction or discharge operation starting time for the suction and discharge mechanism and the fluid movement starting time for column tips, the offset of suction or discharge operation quantity and the suction or discharge quantity of the fluid for the column tip after achieving the operation quantity, and the details of the reaction of the packing with substances contained in the subject fluid, in order to correct the difference between the targeted suction or discharge quantity at the completion of the suction or discharge and the suction or discharge quantity of the fluid for the column tip after completion of the operation.

A fourteenth aspect of the invention is a column tip processing method, wherein the optimum parameter determining step determines, based on a standard structural requirement for which one or more standard values are set for at least a part of the plurality of the items of the structural requirement generated corresponding to the predetermined standard column tips and the standard processing contents and a standard processing requirement for which one or more standard values are set for at least a part of the plurality of the items of the processing requirement, an optimum parameter corresponding to structural requirements and processing requirements other than the standard structural requirements and the standard processing requirement for those other than the predetermined standard column tips and processing contents.

A fifteenth aspect of the invention is a column tip processing method according to Claim 10, comprising, after the discharge step, a step for washing the packing enclosed in the column tip by allowing a washing fluid as a subject fluid to be suctioned into and discharged from the column tip and an elution step for introducing an eluent into the column tip whereby eluting the processing subject fluid-carried biological substances which were adsorbed to, captured by and reacted with or bound to the packing.

A sixteenth aspect of the invention is a column tip processing method, wherein, in the contact step, a temperature raising and lowering step for raising and lowering the temperature of the subject fluid based on the processing requirement is provided, and the raising and lowering of the temperature is conducted by means of a relative movement between the nozzle and the temperature raising and lowering vessel provided on the stage.

A seventeenth aspect of the invention is a column tip processing method, further including a detachment step for detaching the column tips fitted to the nozzle, wherein the detaching step is conducted by means of a relative movement between the detaching part provided on the stage and the nozzle based on the structural requirement and processing requirement.

When, upon the fitting step, the column tip is subjected to a step for preventing the fall down from the nozzle for the purpose of preventing the fall off from the nozzle for example by engaging a fall off preventing member in the form of a clamp or a comb with the protrusion or the stage of the column tip, it is required, before the detaching step, to pass through a step for cancelling the fall off prevention by breaking the engagement. Breaking the engagement may be accomplished for example by moving the nozzle.

An eighteenth aspect of the invention is a column tip processing method, wherein, after the detaching step, fitting of at least one said column tip of another type, one filter tip connectable to the nozzle, or a dispensing tip housed on the stage is conducted, based on the structural requirement and processing requirement, by means of a relative movement between the nozzle and the housing part in which the column tip, filter tip or dispensing tip is housed.

A nineteenth aspect of the invention is an optimum parameter generating program stored on a non-transitory computer readable medium, for a column tip processing device including: a nozzle head having a single or multiple-channeled nozzle; a suction and discharge mechanism conducting suction or discharge of a gas via the nozzle; one or more types of column tips each having a tip-shaped vessel having a fitting opening to be fitted to the nozzle and a hollow end through which a fluid can flow in or out in response to the suction or discharge of the gas and a packing enclosed in the tip-shaped vessel; a stage provided with a fluid housing part group into which the hollow end can be inserted and which houses or can house various solutions; and moving means for moving the nozzle head relatively to the fluid housing part group, wherein the optimum parameter generating program incorporates one or more column tips fitted to the nozzle and a designating data which designates the processing conducted using the column tips, generates, based on the designating data, a structural requirement data relating to corresponding column tip structure and a processing requirement data relating to the processing contents involving one or more types of subject fluids subjected to the suction or discharge of the column tips included in corresponding processing, and determines, based on the requirements generated, optimum parameter data prescribing quantities, pressure, flow rate, the number of cycles, time or position of the suction or discharge by the nozzle for the suction and discharge mechanism and the moving means.

A twentieth aspect of the invention is an optimum parameter generating program stored on a non-transitory computer readable medium, wherein the packing is enclosed in the tip-shaped vessel using at least one filter provided in a manner to partition the tip-shaped vessel, the structural requirement data include a plurality of items relating to the structure of the member or the tip-shaped vessel to be fitted to the nozzle, the structure of the filter or the morphology or nature of the packing enclosed, and the processing requirement data include a plurality of items relating to the processing contents including each housing position, nature or quantity of one or more types of the subject fluids subjected to the suction or discharge of the column tips.

A twenty first aspect of the invention is an optimum parameter generating program stored on a non-transitory computer readable medium, wherein the optimum parameter decision determines an optimum parameter data relating to suction or discharge, based on the generated corresponding structural requirement data and processing requirement data for each of the column tips and processing contents, while considering the difference in time between the suction or discharge operation starting time for the suction and discharge mechanism and the fluid movement starting time for column tips, the offset of suction or discharge operation quantity and the suction or discharge quantity of the fluid for the column tip after achieving the operation quantity, and the details of the reaction of the packing with substances contained in the subject fluid, while considering the suction or discharge parameter and the difference in time between the suction or discharge operation starting time and the fluid movement starting time for column tips, the offset of suction or discharge operation quantity and the suction or discharge quantity of the fluid for the column tip after achieving the operation quantity, and the details of the reaction of the packing with substances contained in the subject fluid.

A twenty second aspect of the invention is a column tip processing device including: a nozzle head having a single or multiple-channeled nozzle; a suction and discharge mechanism conducting suction or discharge of a gas via the nozzle; one or more types of column tips each formed from a tip-shaped vessel having a fitting opening fitted or capable of being fitted to the nozzle and a hollow end through which a fluid can flow in or out in response to the suction or discharge of the gas and each accompanied with a packing enclosed in the tip-shaped vessel, or one or more types of filter tips each formed from the tip-shaped vessel and having a filter therein provided in a manner to partition between the fitting opening and the hollow end; a stage provided with a plurality of fluid housing parts into which the hollow end can be inserted and which houses or can house various solutions and a tip housing part group capable of housing the column tips or filter tips; moving means for moving the nozzle head relatively to the fluid housing part group; and a detaching part for detaching the column tip or filter tip fitted to the nozzle, wherein the control of the fitting and detachment of the column tip or filter tip is conducted on the suction and discharge mechanism and the moving means based on the processing requirement relating to the column tip and filter tip.

A twenty third aspect of the invention is a column tip processing device, including one or more types of dispensing tips formed with the tip-shaped vessel and capable of adsorbing magnetic particles onto an inner wall by means of a magnetic field given internally and magnetic means provided in the nozzle head and capable of allowing a magnetic field to be applied to or removed from the inside of the dispensing tip fitted, wherein the dispensing tips can be housed in the tip housing part group provided on the stage, the detaching part can detach the dispensing tips, and the control of the fitting and detachment of the dispensing tip, by the controlling part, is conducted on the suction and discharge mechanism and the moving means based on the processing requirement relating to the dispensing tip.

A twenty fourth aspect of the invention is a column tip processing device, wherein said one or more types of the column tips comprise gel filtration column tips or affinity column tips.

As used herein, a "gel filtration column tip" is, among column tips, a tip whose packing enclosed is a gel for a gel filtration chromatography such as Sephadex or Sephacryl, and serves for a processing in such a manner that a subject fluid is introduced from the fitting opening of the column tip and the subject fluid is allowed to pass through the packing by gravity or under pressure whereby discharging the liquid to the outside of the column tip. Only one filter is provided under the packing. The "affinity column tip" means a tip enclosed with a gel for an affinity chromatography to which a substance reacting specifically with an intended biological substance such as an antibody, antigen, nickel, glutathione and the like is bound.

A twenty fifth aspect of the invention is a column tip processing device, wherein the nozzle head is provided with a fall off preventing part which prevents the fall off from the nozzle by engaging with the tip-shaped vessel of the column tip fitted to the nozzle, the control of the fall off prevention and a cancellation thereof by the fall off preventing part is conducted on the moving means based on the processing requirement.

A twenty sixth aspect of the invention is a column tip processing method, in which a stage houses one or more types of column tips each having a tip-shaped vessel having a fitting opening fitted to a single or multiple-channeled nozzle, conducting suction or discharge of a gas by a suction and discharge mechanism and a hollow end through which a fluid can flow in or out in response to the suction or discharge of the gas and a packing enclosed in the tip-shaped vessel, or one or more types of filter tips each having the tip-shaped vessel and a filter provided in a manner to partition between the fitting opening and the hollow end, and, which comprises, based on a processing requirement relating to the processing contents involving one or more types of subject fluids subjected to the suction or discharge of the column tips or filter tips, a fitting step for fitting a column tip or filter tip to the nozzle at the fitting opening by moving the nozzle relatively between it and the housing parts of the column tip or filter tip housed; a suctioning and discharging step for inserting the hollow end into the fluid housing part by a relative movement between one or more fluid housing part housing the subject fluid and the nozzle whereby suctioning and discharging the subject fluid; a detaching step for detaching column tips or filter tips fitted to the nozzle; and, a re-fitting step for conducting fitting of at least one said column tip of another type or one filter tip housed on the stage to the nozzle is conducted by means of a relative movement between the nozzle and the housing part in which the column tip or filter tip is housed.

A twenty seventh aspect of the invention is a column tip processing method which houses, on the stage, one or more types of dispensing tips each formed from a tip-shaped vessel and capable of adsorbing magnetic particles onto inner wall by means of a magnetic field given internally, wherein the processing requirement relates to the processing contents involving one or more types of subject fluids subjected to the suction or discharge of a dispensing tip, the fitting step comprises a step for fitting the dispensing tip to the nozzle, the suction or discharge step comprises a step for suctioning and discharging the subject fluid while applying a magnetic force into the dispensing tip, wherein the detaching step comprises a step for detaching the dispensing tip fitted to the nozzle, and the re-fitting step conducts fitting of the dispensing tip to the nozzle is conducted by means of a relative movement between the nozzle and the housing part in which the dispensing tip is housed.

A twenty eighth aspect of the invention is a column tip processing method, wherein said one or more types of the column tips comprise gel filtration column tips or affinity column tips.

A twenty ninth aspect of the invention is a column tip processing device including: a nozzle head having a single or multiple-channeled nozzle; a suction and discharge mechanism conducting suction or discharge of a gas via the nozzle; one or more types of column tips each formed from a tip-shaped vessel having a fitting opening fitted or capable of being fitted to the nozzle and a hollow end through which a fluid can flow in or out in response to the suction or discharge of the gas and each accompanied with a packing enclosed in the tip-shaped vessel; a stage provided with a plurality of fluid housing part group into which the hollow end can be inserted and which houses or can house various solutions; and moving means for moving the nozzle head relatively to the fluid housing part group, wherein, in the fluid housing part group, a buffer solution having a plurality of different concentrations arranged at a certain concentration difference from each other along with a certain concentration gradient with regard to a certain salt is housed.

The "arranged" form may for example be a matrix form or a linear form.

A thirtieth aspect of the invention is a column tip processing device, wherein on the stage, the column tips, and dispensing tip are housed, and a detaching part for detaching the fitted dispensing tip or column tip from the nozzle are provided.

A thirty first aspect of the invention is a column tip processing method, for one or more types of column tips each having a tip-shaped vessel having a fitting opening, fitted to a single or multiple-channeled nozzle, conducting suction or discharge of a gas by a suction and discharge mechanism and a hollow end through which a fluid can flow in or out in response to the suction or discharge of the gas and a packing enclosed in the tip-shaped vessel, which includes: an adsorption step for allowing an intended biological substance to be adsorbed onto the packing by means of suction and discharge of a subject fluid containing the intended biological substance; and a contacting step for housing, as a subject fluid subjected to the suction or discharge of said two or more column tips, a buffer solution having a plurality of different concentrations arranged at a certain concentration difference from each other along with a certain concentration gradient with regard to a certain salt, and inserting one or more column tips into one or more said fluid housing part to effect suction or discharge, whereby bringing the packing into contact with the buffer solution.

A thirty second aspect of the invention is a column tip processing method, wherein generation and housing of the buffer solution is conducted using a dispensing tip fitted to the nozzle.

Advantage of the Invention

According to the first, tenth, or nineteenth aspect of the present invention, for one or more types of column tips, based on a structural requirement relating to the structure of the column and a processing requirement relating to the processing contents involving one or more types of subject fluids subjected to the suction or discharge, quantities, pressure, flow rate, and the like of the suction or discharge by the nozzle are determined. As a result, a highly efficient processing can be conducted by bringing the subject fluid into contact with the packing in a manner of suction or discharge which is optimum for the column tip having a complicated structure containing various types of packing. In addition, by conducting the suction or discharge with a small amount of the liquid including only the subject fluid without using a mobile medium including a large quantity of a buffer solution and without diluting an intended biological substance, a high efficiency with a small-scaled device can be accomplished.

It is also possible, based on the structural requirement and processing requirement, a continuous automatic processing including fitting of column tips to the nozzle, selection of optimum column tips, selection of a necessary subject fluid, transportation to the position of housing, and optimum suction or discharge can be accomplished.

According to the second, eleventh, or twentieth aspect of the present invention, by taking the structure of the tip-shaped vessel, the structure of the filter or the shape or the nature of the packing into account as structural requirements with regard to the column tips, and also by taking the nature and the quantity of the subject fluid, the factors serving as a resistance against the suction or discharge of the fluid are contemplated, whereby controlling optimum pressure, flow rate, cycles or time period of the suction or discharge.

According to the third, twelfth, or nineteenth aspect of the present invention, a structural requirement relating to the designated column tips and a processing requirement relating to the designated processing are generated, and based on such structural requirement and processing requirement an optimum parameter is determined. Accordingly, only a designation by a user of the column tips and the processing enables various structural requirements and the various requirements for the processing to be taken into account automatically, whereby allowing the optimum parameters to be readily obtained.

According to the fourth, thirteenth, or twenty first aspect of the present invention, since an optimum parameter is determined based on the difference in time between the operation designating time and the fluid movement starting time, the suction or discharge operation quantity, and the offset of the suction or discharge quantity of the fluid for the column tip after achieving the operation quantity, the optimum parameter can quickly and readily be obtained, and various cases can readily be handled just by exchanging the reference table.

According to the fifth or fourteenth aspect of the present invention, by prescribing a standard structural requirement and a standard processing requirement corresponding to the predetermined standard column tip and the standard processing contents, an optimum parameter corresponding to other structural requirements and processing requirements can readily be obtained. Because of a simple construction applicable to various column tips and processings, a wide range of use is possible.

According to the sixth or sixteenth aspect of the present invention, by conducting the control of the temperature of the subject fluid to be in contact with the packing, by conducting the control of the temperature of the subject fluid to be in contact with the packing by means of the movement to the temperature raising and lowering vessel based on the processing requirement, the temperature control and the suction or discharge can be conducted independently in parallel, whereby allowing the suction or discharge to be conducted at an optimum temperature. In addition, since the temperature is controlled by moving, the control can readily be conducted.

According to the seventh or seventeenth aspect of the present invention, by providing a detaching part for a column tip once fitted to a nozzle, a plurality of s of column tips, filter tips or dispensing tips can sequentially be exchanged by a single device, or can simultaneously be employed in combination, whereby allowing diverse processings to be conducted continuously and automatically.

According to the eighth aspect of the present invention, by providing necessary reagents preliminarily in a pre-packed vessel, the necessary reagents can be handled readily, rapidly and efficiently, only by moving the nozzle, in a best and highly reliable state when necessary.

According to the ninth aspect of the present invention, by engaging with a tip-shaped vessel fitted to a nozzle, a column tip is prevented from falling off from the nozzle of the column tip. Therefore, it becomes possible to apply a high pressure, against the presence of the packing or the filter, to the column tip upon discharge, whereby enabling application to various column tips and filter tips. The cancellation of the fall off prevention can readily and automatically be conducted by movement of the moving means. As a result, the column tip or the like can be detached, and various column filters or other tips can be employed as being exchanged or in combination.

According to the fifteenth aspect of the present invention, by a step for washing the packing and eluting the biological substance once adsorbed onto the packing, contaminants which were not adsorbed onto the packing can surely be removed by repeating suction and discharge, and the biological substance adsorbed on the packing can only be recovered surely and efficiently.

According to the twenty second or twenty sixth aspect of the present invention, since the column tip or the filter tip fitted to the nozzle can be detached and then other types of tips can further be fitted, a plurality of types of column tips or filter tips can sequentially be exchanged, or can simultaneously be employed in combination in a single device, whereby allowing diverse processings to be conducted continuously and automatically.

According to the twenty third or twenty fifth aspect of the present invention, since the dispensing tip fitted can further be detached and then other types of tips can further be fitted, or other types of the tips are detached and the dispensing tip can be fitted to conduct a processing. Accordingly, a plurality of types of tips including dispensing tips can sequentially be exchanged, or can simultaneously be employed in combination in a single device, whereby allowing diverse processings, including absorption using a magnetic field, to be conducted continuously and automatically.

According to the twenty fourth or twenty seventh aspect of the present invention, by using the above type of the column tips as a column tip, for example by using a dispensing tip and a gel filtration column tip, a magnetic particle-based fusion protein purification and a pretreatment of gel filtration column tip-based protein analysis can continuously be performed. In addition, by combining the affinity column tip and the gel filtration column tip, the affinity column tip is used for removing the major proteins, whereby enabling the extraction of the useful proteins continuously. By combining the affinity column tip, the gel filtration column tip and the filter tip, a pretreatment of a protein analysis sample can continuously be conducted.

According to the twenty ninth or thirty first aspect of the present invention, instead of a conventional separation based on the specificity and the nature of a protein resulting from a difference in the concentration along with the time, by housing a set of a plurality of buffer solutions having differences in concentration from each other along with a gradient of the concentration preliminarily in fluid housing parts and then moving the column tips between the fluid housing parts, or by inserting a plurality of the column tips at once into the fluid housing parts, or by combining these procedures, the concentration at which the intended biological substance is eluted surely at a high accuracy with the desired concentration difference.

According to the thirtieth or thirty second aspect of the present invention, since a set of a plurality of buffer solutions having differences in concentration from each other along with a gradient of the concentration can be subjected to fitting of dispensing tips to a nozzle of an identical device, the processing can readily and continuously be conducted.

BEST MODE FOR CARRYING THE INVENTION

Figure 1:
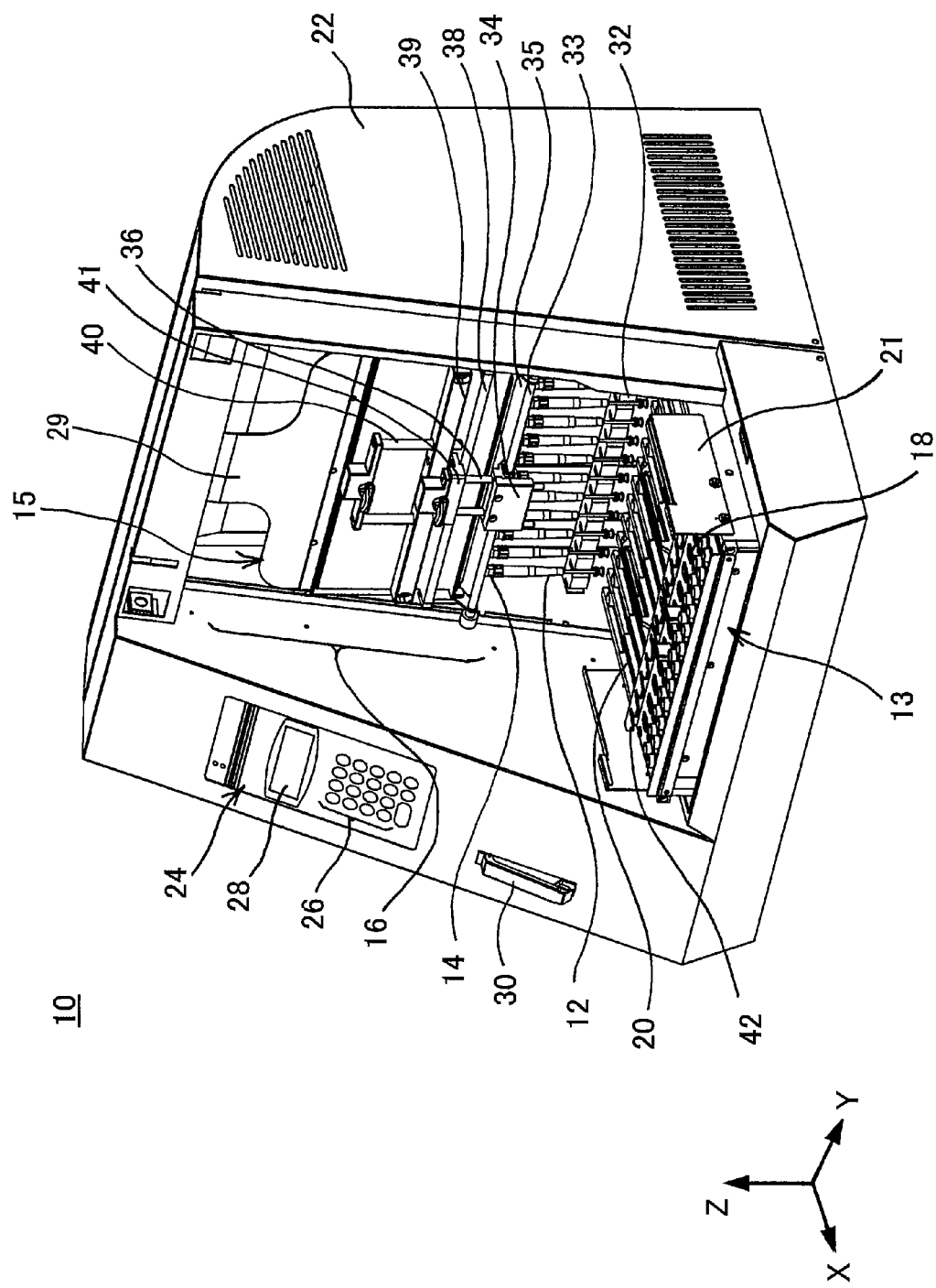
FIG. 1 is a perspective view of a column tip processing device according to a first embodiment of the invention.

A column tip processing device 10 according to a first embodiment of the invention is described with reference to FIGS. 1 to 3.

The column tip processing device 10 includes a nozzle head 15 having a suction and discharge mechanism 16 for conducting the suction and discharge of a gas and a multiple-channeled (in this case, 12-channeled) nozzle 14 to which column tips 12 are fitted as described below and which is arranged linearly along with Y axis for allowing the gas to be suctioned into or discharged from these column tips 12, a stage 13 having a housing part group 20 having, in the form of a row, various fluid housing part which houses various samples or reagent-containing solutions to be suctioned into the column tips 12 or discharged from the column tips 12 or a tip housing part 61 which houses various column tips including the column tips 12, a moving mechanism 97 as a moving means for moving the nozzle head 15 and the housing part group 20 relatively in a horizontal direction (in this case, in the direction of X axis) and in a vertical direction (in the direction of Z axis), an operation panel 24 and a lid-fitted IC card insertion port 30 for designating the column tips and the processing contents and for entering various data, a detachment plate 42, provided on the stage 13, as a detaching part for detaching the column tips 12 from the nozzle 14, and a case 22 in which the column tips and respective components are housed in a manner allowing them to be operated externally. Here, the X axis, Y axis and Z axis together form a three dimensional rectangular coordinate system. The operation panel 24 and the lid-fitted IC card insertion port 30 together with an information processing part (not shown) constitute a controlling part.

On the operation panel 24, a liquid crystal display 28 and an input keyboard 26 are provided. On the nozzle head 15, 12 magnets, as a magnetic force means for applying a magnetic force to the inside of a dispensing tip (110, see FIG. 8) when this dispensing tip is fitted a nozzle 14, are provided as being arranged on a rod-shaped member extending longitudinally (in the direction of the Y axis in the figure) at an interval of the arrangement of the nozzle 14 while capable of being in contact with and released from the dispensing tip in a back-and-forth direction (in the direction of the X axis in the figure).

A fall off preventing parts 33 to 38, 40, 44 and 46 serve to prevent the fall off of the column tips 12, that are fitted as being engaged with the nozzle 14, from the nozzle 14, or serve to cancel such a fall off prevention, and are provided in such a manner that they move in concert with the nozzle head 15 movable in the direction of the Z axis. This fall off preventing part is provided since a high pressure should be applied by the suction and discharge mechanism to the column tips 12 because of the structure inside of the column tips 12 serving as a resistance to a fluid, such as the packing, filters and the like. On the stage 13, two wall plates 21 extending in the direction of the X axis as sandwiching the housing part group 20 are provided. A screen 29 is to hide a P axis motor 49 and the like provided in the back.

Figure 2:
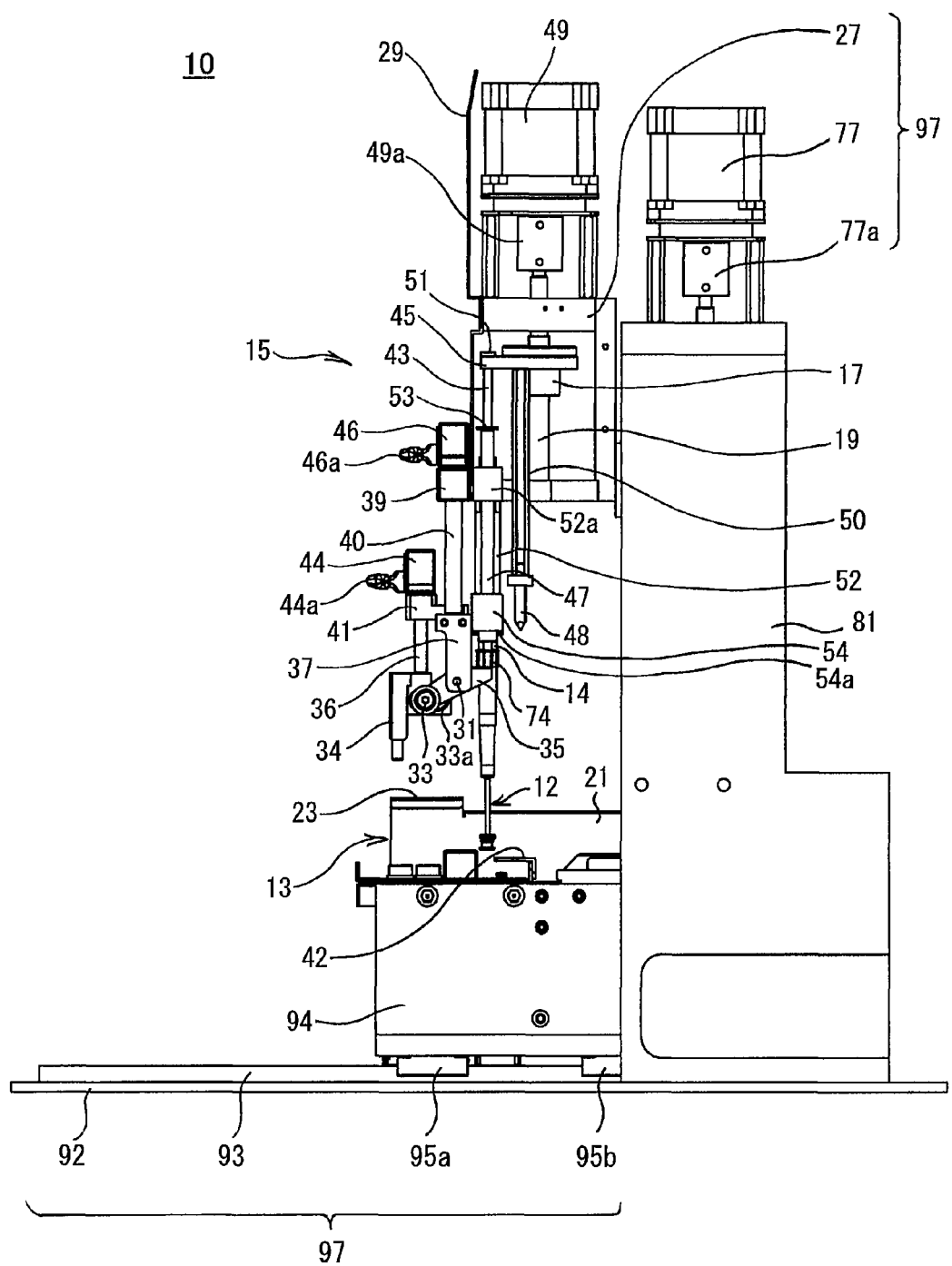
FIG. 2 is a side view of a nozzle head of the column tip processing device according to the first embodiment of the invention.

FIG. 2 shows a side view of the major part including the nozzle head 15 placed in the column tip processing device 10.

The 12 individual nozzles 14 of this nozzle head 15 are supported by a nozzle supporting member 54 as being arranged along with the longitudinal direction thereof.

Above each individual nozzle 14, 12 cylinders 47 in communication with the nozzles 14 are provided, and inside of each cylinder 47 a plunger 43 is provided pivotally each in the direction of the axis, and the top 51 of the upper end of the plunger 43 is supported as being fixed on the driving plate 45 in a state that the top 51 is protruded over this driving plate 45 which is driven up and down by the P axis motor 49 for the suction and discharge which is provided as being supported by a Z axis moving body 27 provided in the nozzle head 15. On this driving plate 45, 12 hexangular prism-shaped hexangular posts 50 are attached in the position at a certain distance in the direction of the X axis from the plunger row where the plungers 43 are arranged in the direction of the Y axis while being arranged in the direction of the Y axis at an interval of the arrangement identical to that of the plungers 43 and also being allowed to extend downward. At the lower end of the hexangular post, a puncturing needle 48 for puncturing a thin film for example of a prepack is protruded downwardly.

The driving plate 45 is fixed to a nut part 17 which is engaged with a ball screw 19 driven to rotate via a coupler 49a by the P axis motor 49 for suction and discharge provided as being supported by the Z axis moving body 27 of the nozzle head 15 supported movably in the direction of the Z axis relatively to a fixed case 22 of the column tip processing device 10, and also which moves up and down in response to the rotation of this ball screw 19. This ball screw 19 is supported coaxially to the Z axis moving body 27 by means for example of a bearing. This Z axis moving body 27 is provided movably in the direction of the Z axis as being guided by a Z axis moving body supporting platform 81 provided as being fixed to the case 22. On the top of this Z axis moving body supporting platform 81, a Z axis motor 77 is provided, and serves to move this Z axis moving body 27 in conjunction via a coupler 77a with the ball screw which engages with the nut part provided as being fixed on the Z axis moving body 27. The stage 13 is formed above an X axis moving body provided movably in the direction of the X axis as being set as described above. On a base 92 of the case 22, a linear motion rail 93 is laid in the direction of the X axis, and beneath the X axis moving body 94, linear motion guides 95a and 95b on which a plurality of balls are supported as being capable of rotating and circulating are provided, and are capable of moving smoothly as being guided by the linear motion rail 93. Here, the Z axis moving body 27, the Z axis moving body supporting platform 81, the X axis moving body 94 and the rail 93 and the like correspond to the moving means 97.

On this driving plate 45, a light shielding plate (not shown) is provided as being extending vertically. When the driving plate 45 reaches the upper limit of the plunger 43, then blocks the light from a light emitting element provided as being fixed to the case 22, whereby preventing the arrival at the light receiving element.

Beneath each cylinder 47 described above, a horizontal plate 54a having pores (not shown), whose size allows the passage of the nozzle but does not allow the passage of the column tip 12 or the dispensing tip 110 (see FIG. 8), provided under the nozzle supporting member 54 along with the longitudinal direction of this nozzle supporting member 54 is provided. On each of the both ends of this horizontal plate 54a, a tubular post 52 is each provided which supports the horizontal plate for detaching the dispensing tips (not column tips). The 12 cylinders 47 are fixed at their upper ends by a cylinder supporting member 52a while being supported to extend downward therefrom, and the post 52 penetrates this cylinder supporting member 52a to protrude upward therefrom, and the upper end of the post 52 is supported by a post supporting tube 53 as being fixed. The 12 plungers 43 penetrate the post supporting tube 53, and are slidable independently. The cylinder supporting member 52a is provided in such a manner that it moves in conjunction with the nozzle head 15.

The driving plate 45 functions, when conducting the suction and discharge of a gas or when puncturing a thin film of such as a prepack using the puncturing needle 48, by moving back and forth on the plunger 43 between the upper limit position and the upper end of the post supporting tube 53, while the driving plate 45 can go down further from the upper end of the post supporting tube 53 to reach the lower limit position. In such a case, the driving plate 45 goes down together with the post supporting tube 53 whereby pushing the post 52 and allowing the horizontal plate to go down, whereby allowing the dispensing tip once fitted (not used for the column tips) to be drawn down apart from the nozzle 14. The detachment of the column tip 12 from the nozzle 14 is discussed below.

Based on FIGS. 1 and 2, the mechanism possessed by the fall off preventing part which prevents the column tips 12 from falling off from the nozzle 14 is described.

In this fall off preventing part, a fall off preventing member 35 having 12 approximately semicircular notches (not shown) arranged in the positions and at an interval of the arrangement identical to that of the column tips 12 in the direction of the Y axis is supported rotatably on a horizontal rod 33. The size of each notch is slightly larger than the diameter of the tube having a large diameter 64 of the column tip 12 and smaller than the outer diameter including the thickness of a protruding streak 74 of this column tip, and in this manner the column tip 12 can be supported at the position of this protruding streak 74. This horizontal rod 33 is provided in such a manner that it moves in conjunction with the nozzle head 15, and this horizontal rod 33 is provided in such a manner that it can move up and down along with the guide rail provided as being fixed in the case 22. This horizontal rod 33 is kept in a rod supporting member 34 in such a manner that it penetrates a oval hole 34 which allows the horizontal rod 33 to rotate and to move over a slight distance in the direction of the X axis. In this rod supporting member 34, two guide parts 36 penetrate the anchoring block 41 formed from a permanent magnet and extend thereover, and on the top of it an upper end part 44 formed from a magnetic body is provided. On the upper end part 44, a knob 44a for releasing the close contact with the anchoring block 41 due to the magnetic force is provided. In the state where the fall off preventing member 35 is engaged with the column tip 12 whereby preventing the fall of the column tip, the upper end part 44 is in a close contact with the anchoring block 41 due to the magnetic force and gravity, as shown in FIG. 2.

In the fall off preventing member 35, in the middle between the end in contact with the column tip 12 and the horizontal rod 33, the fall off preventing member 35 is supported at its axis rotatably on an inverted L-shaped member whose side view is in the shape of an inverted L via a pin 31. This inverted L-shaped member 37 is provided on each of the both ends of an anchoring block supporting member 38 which support the anchoring block 41 which is formed as extending in the direction of the Y axis similarly to the nozzle supporting member 54. Above this anchoring block supporting member 38, 2 upwardly extending guide parts 40 are formed from a permanent magnet, penetrate an anchoring horizontal rod 39 fixed on the Z axis moving body 27 of the nozzle head and extend thereover, and on the top of it an upper end part 46 formed from a magnetic body is provided. In addition, on this upper end part 46, a knob 46a for releasing the close contact with the anchoring horizontal rod 39 due to the magnetic force is provided. In the state where the fall off preventing member 35 is engaged with the column tip 12 whereby preventing the fall of the column tip, the upper end part 46 is in a close contact with the anchoring horizontal rod 39 due to the magnetic force and gravity, as shown in FIG. 2.

In order to release the state of the engaging of the fall off preventing member 35 with the column tip 12, thus, the state of the fall off prevention, the X axis moving body 94 is moved in the direction of the X axis, whereby moving the nozzle head 15, by means of the moving mechanism, relatively in the direction of the X axis to come above a wall part 23 for release, among the wall plate 21, which is mounted as being slightly higher than others in the direction of the Z axis, and thereafter using the moving mechanism the nozzle head 15 is moved downward in the direction of the Z axis. As a result, the horizontal rod 33 is brought into contact with the wall part 23 for release, and upon a further downward movement, this horizontal rod 33 receives an upward force whereby rotating around the pin 31 as an axial fulcrum, resulting in release of the notch of the fall off preventing member 35 from the protruding streak 74. Upon this, since the parts other than the horizontal rod 33 and the part attaching thereto are going to move further downward, the upper end part 44, which are attached via the rod supporting member 34 and a guide member 36 to this horizontal rod 33 is released from the anchoring block 41. At the same time, the upper end part 46, which are attached via inverted L-shaped member 37 and a guide member 40 to this horizontal rod 33 is released from the anchoring horizontal rod 39.

On the other hand, in order to validate the fall off prevention, the Z axis moving body 27 of the nozzle head 15 is raised in the direction of the Z axis, whereby first raising the parts other than the horizontal rod 33 and the part attaching thereto, and the upper end part 44 is brought into a close contact with the anchoring block 41 due to it's own weight and a magnetic force, and the upper end part 46 is brought into a close contact with the anchoring horizontal rod 39 due to it's own weight and a magnetic force, and simultaneously the horizontal rod 33 is released from the wall part 23 for release, resulting in engagement of the fall off preventing member 35 with the protruding streak 74 of the column tip 12, whereby accomplishing the fall off prevention.

Figure 3:
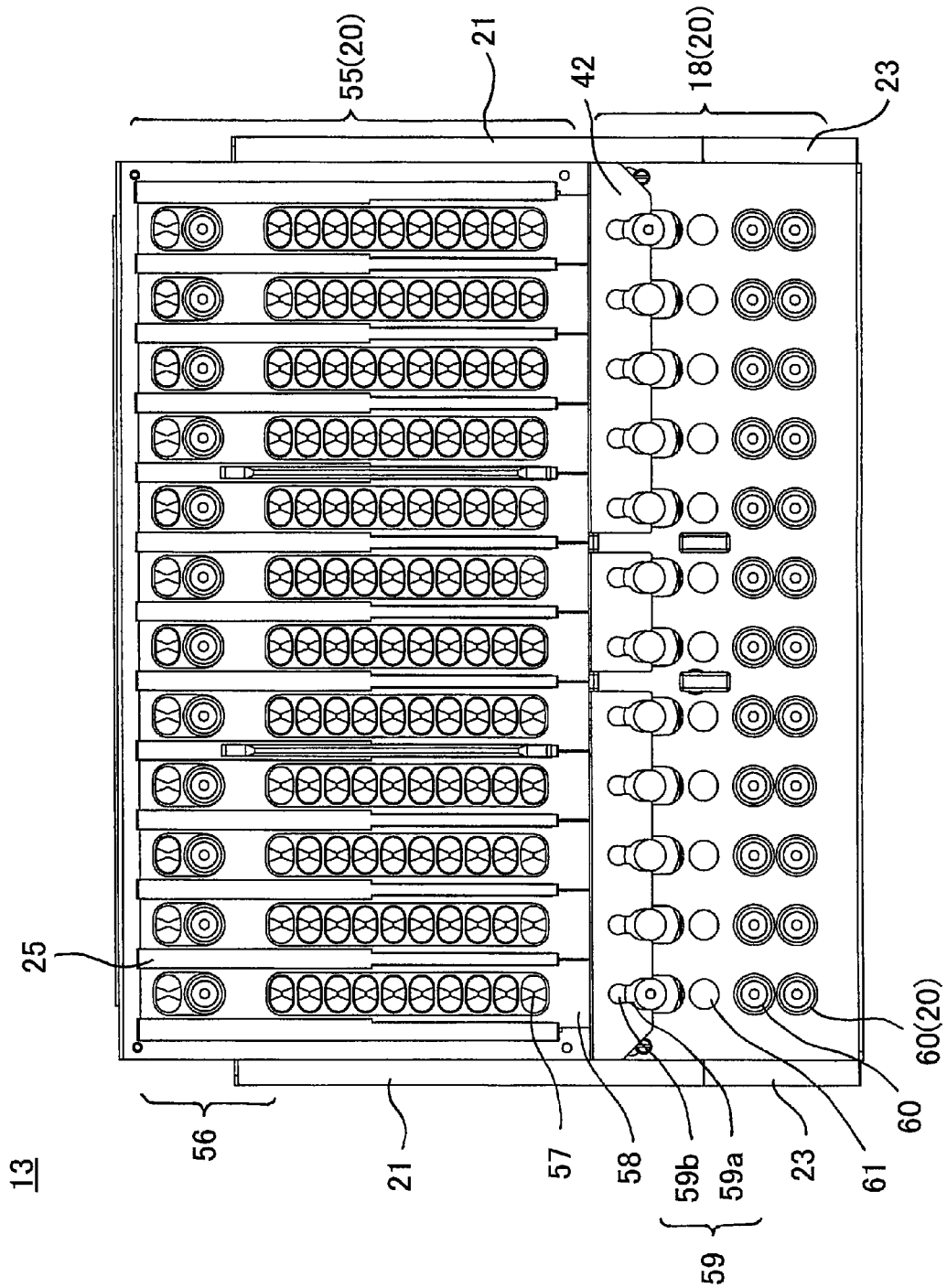
FIG. 3 is a planar view of the column tip processing device according to the first embodiment of the invention.

FIG. 3 shows the stage 13 of the column tip processing device 10. On this stage 13, a reagent rack 55, as the housing part group 20, having 12 groups of reagent prepack cartridges 58 including a plurality of fluid housing parts in which a certain reagent solution has preliminarily be housed and which has been covered with thin films and a tip rack 18 having a 4-row 12 tip housing part 61 capable of housing the column tips 12 or the dispensing tips are provided.

In the reagent prepack cartridge 58, a plurality of fluid housing parts (in this case, 10) 57 and heat block parts 56 for heating, and on each of these heat block parts 56, a fluid housing part for the reagent and a sample tube are provided. On the both sides of each reagent prepack cartridge 58, a septum 25 having a certain height is provided.

Among the tip racks 18, lower 2 rows house sample tubes 60. Above the tip housing parts for the upper 1 row, a detachment plate 42 as the detaching part is provided. This detachment plate 42 has 12 holes 59, including holes 59a each having a size enabling the passage of the nozzle 14 but not enabling the passage of the column tip 12 or dispensing tip and holes 59b each having a size enabling the passage of the tube 66 having a small diameter of this column tip 12 but not enabling the passage of other parts, as being arranged on the detachment plate 42 at an interval of the arrangement of the nozzle 14.

Figure 4:
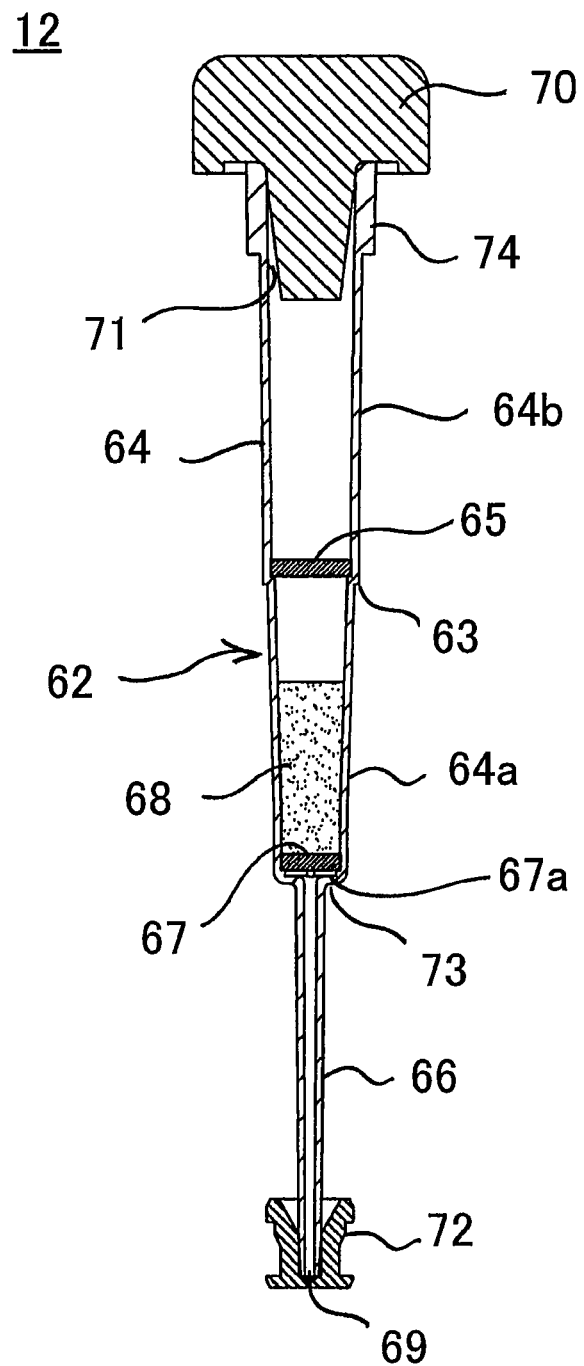
FIG. 4 is a sectional view of a column tip before fitting to the nozzle according to the first embodiment of the invention.

With reference to FIG. 4, the column tip 12 according to the first embodiment is described.

The sectional view of this column tip 12 shown in FIG. 4 is in the state before fitting to the nozzle 14 of the column tip processing device 10.

This column tip 12 has a tip-shaped vessel 62 in which an opening 71 for fitting to be fitted to a nozzle 14 via the nozzle 14 or a member fitted to this nozzle 14 is provided at the upper end and a hollow end 69 through which a fluid can flow in and out is provided at the lower end. This tip-shaped vessel 62 has a tube having a large diameter 64 provided with the fitting opening 71 and enclosed with a packing 68, an approximately cylindrical tube having a small diameter 66 formed as being narrower than this tube having a large diameter 64 and having the hollow end 69 at its end, and a step-like transfer part 73 formed between the tube having a large diameter 64 and the tube having a small diameter 66. The tube having a large diameter 64 has, in its lower side, a packing housing part 64a into which the packing 68 is enclosed, and, in its upper side, a retaining part 64b which is formed as being broader than the packing housing part 64a and which can retain a fluid, as well as a step part 63 formed between this packing housing part 64a and the retaining part 64b. In addition, in the upper part of the outer surface of the tube having a large diameter 64, a plurality of protruding streaks 74 formed in the direction of the axis are provided, and employed for the support by a fall off preventing member 35 as discussed above. The packing 68 (for example, several ten micrometers to 100 micrometers) is enclosed as being sandwiched by a filter 65 provided in the step part 63 and a filter 67 provided in the transfer part 73.

At the bottom of the packing housing part 64a, a plurality of protrusions 67a protruding in the direction of radius relative to the axial line are provided as surrounding the axial line, whereby preventing the filter 67 from being in a close contact.

The packing 68 of this column tip 12 should be stored in contact with an activation maintaining fluid before the processing in order to maintain its activation. Accordingly, the storage is in a state where for preventing any fluid leakage of the opening 71 for fitting is sealed by a lid 70 while the hollow end 69 is sealed by a cap 72.

Upon fitting to the nozzle 14, the lid 70 is removed manually and fitting is established by putting into the nozzle 14, while the cap 72 is removed by inserting the tube having a small diameter 66 of the column tip 12 laterally into the holes 59b of the detachment plate 42, followed by moving the nozzle head 15 upward.

Figure 5:
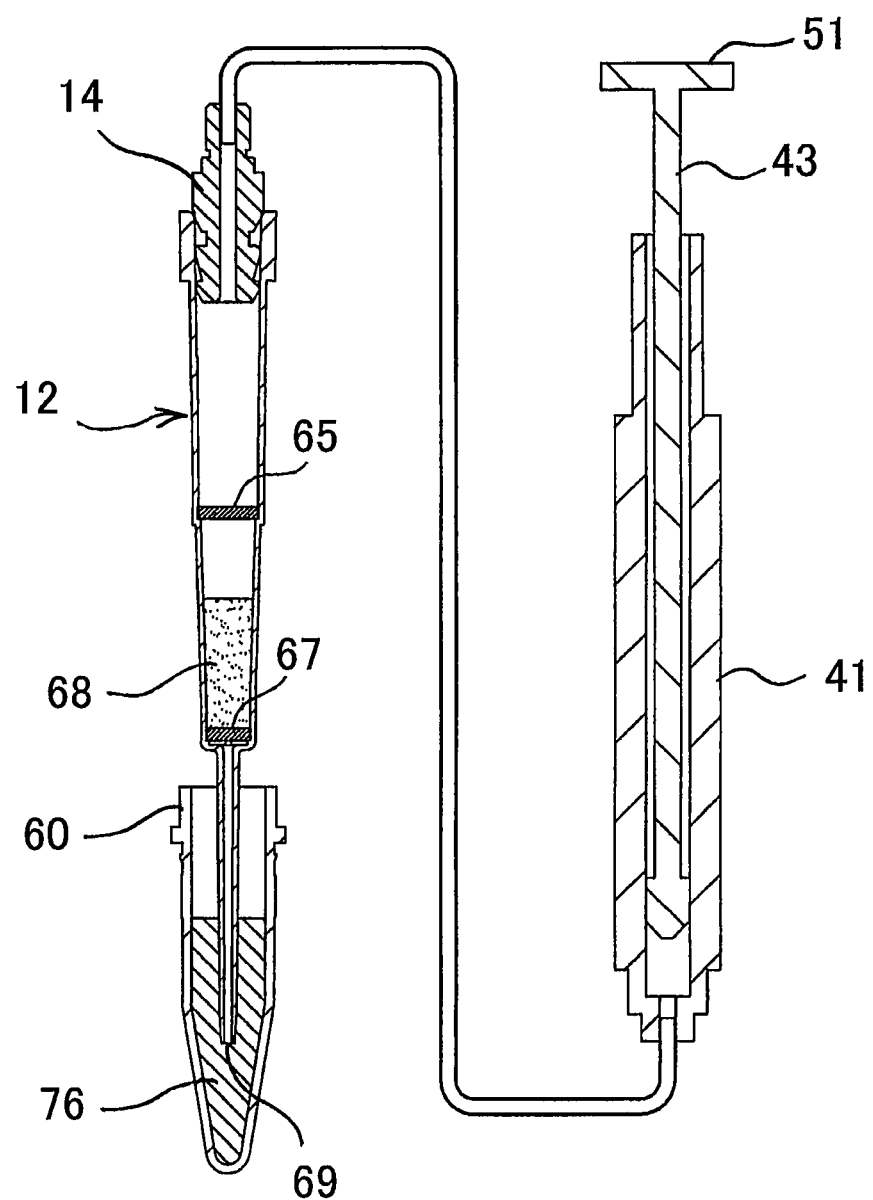
FIG. 5 shows suction and discharge of a column tip according to the first embodiment of the invention.

FIG. 5 shows the state where into the column tip 12 a subject fluid 76 containing an intended biological substance is suctioned via the sample tube 60.

In this case, in the valid column tip region sandwiched between the filter 65 and the filter 67, the entire volume of the packing 68 occupies only about 60% of the capacity of the valid column tip region. In such a case, the quantity of the subject fluid 76 as a subject for suction and discharge is suctioned and discharged repetitively to an extent not exceeding the upper filter 65, whereby establishing the suspension state of the packing 68 with the subject fluid 76 without introducing air, resulting in an enhancement of the contact between the packing 68 and the biological substance contained in the subject fluid 76. Such a procedure is employed mainly when enclosing an affinity gel. An exemplary use is for elution of a purified antibody after allowing a sample to be adsorbed onto the affinity gel.

Figure 6:
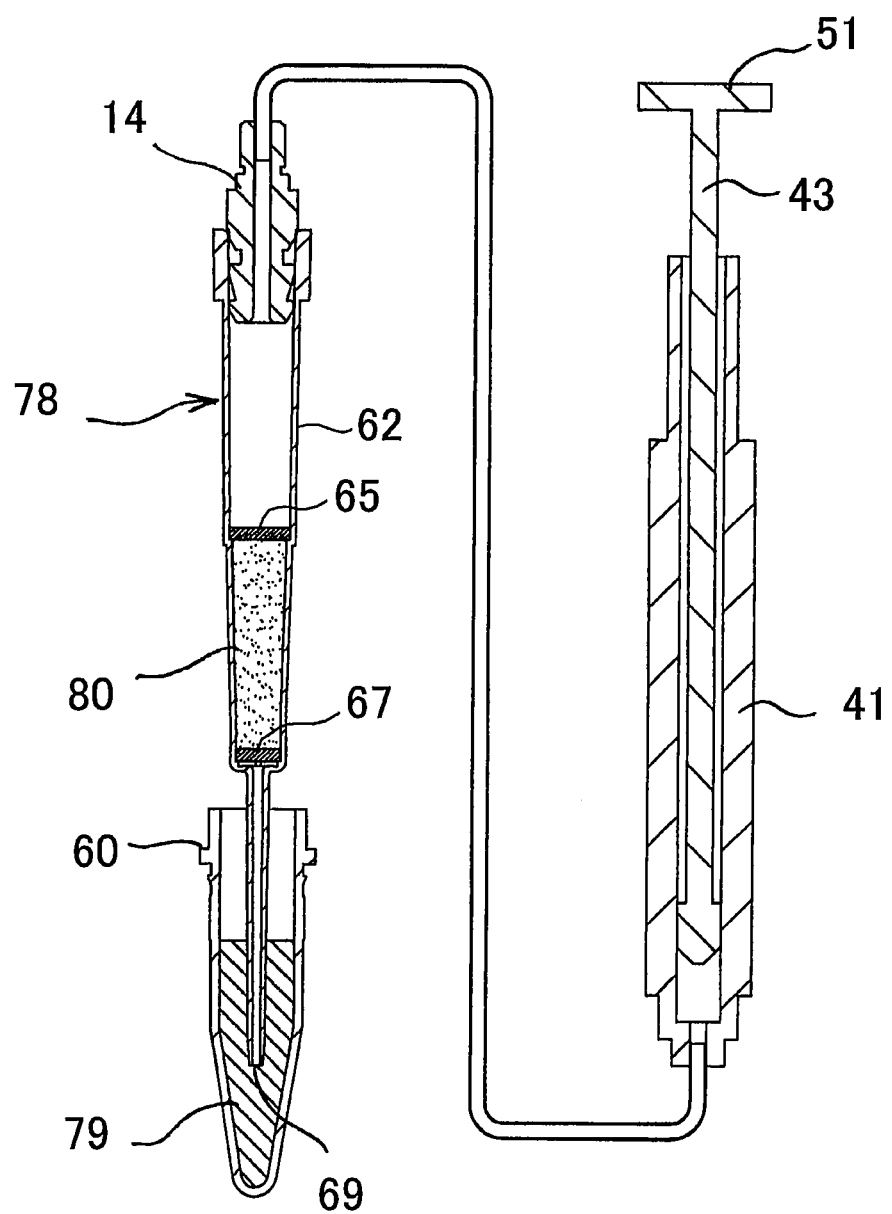
FIG. 6 shows suction and discharge of a column tip according to a second embodiment of the invention.

FIG. 6 shows a case where the column tip 78 has a tip-shaped vessel 62 similar to the column tip 12 having a valid column region sandwiched between the similar filter 65 and filter 67, in which the entire particulate volume of the packing 80 is enclosed as being compressed at a rate of about 100% of the valid column region.

In such a case, suction and discharge can be conducted in such a manner that the suction and discharge fluid quantity exceeds the capacity of the valid column tip region, and such a procedure is employed in a liquid chromatography in which the fractionation is conducted based on the discharge time difference or the number of suction and discharge cycles. In addition, in this case, a microscopic suspension state is considered to be established. For example, a gel filtration chromatography is employed for desalting of the purified antibody as well as removing contaminants.

Figure 7:
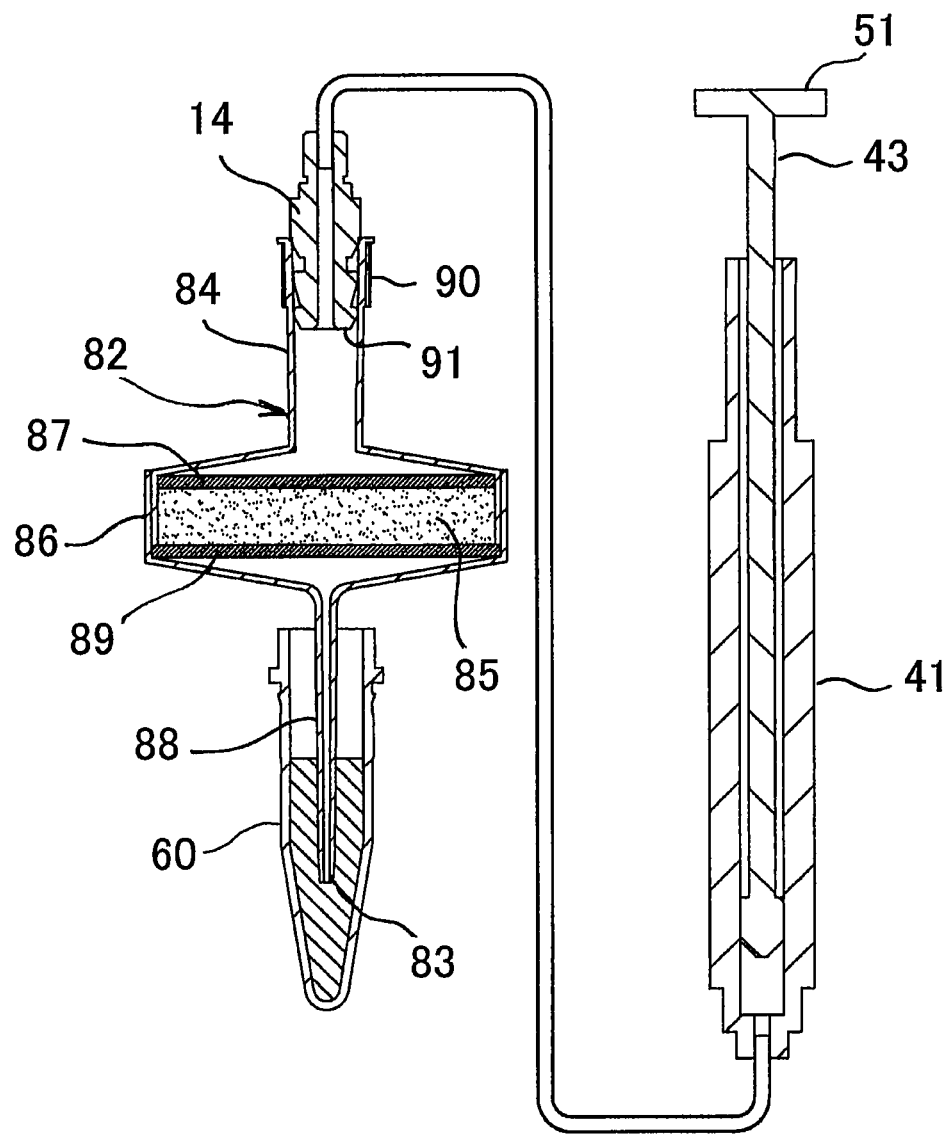
FIG. 7 shows suction and discharge of a column tip according to a third embodiment of the invention.

FIG. 7 shows a spinning top-like or disc-like column tip 82. This column tip 82 has a retaining part 84 having a fitting opening 91 capable of being fitted to the nozzle 14, a hollow disk-shaped packing enclosed part 86 in which the packing 85 is enclosed as being compressed at a rate of about 100% of the capacity of the valid column region of the entire particulate volume, and a narrow tube 88 having a hollow end 83 capable of being inserted into the sample tube 60.

This column tip 82 can reduce the suction and discharge time by making the thickness of the packing 85 in the direction of the axis thinner and increasing the porosity, in the case where the particle size of the packing 85 is small and the pore sizes of the filters 89 and 87 are also small.

Figure 8:
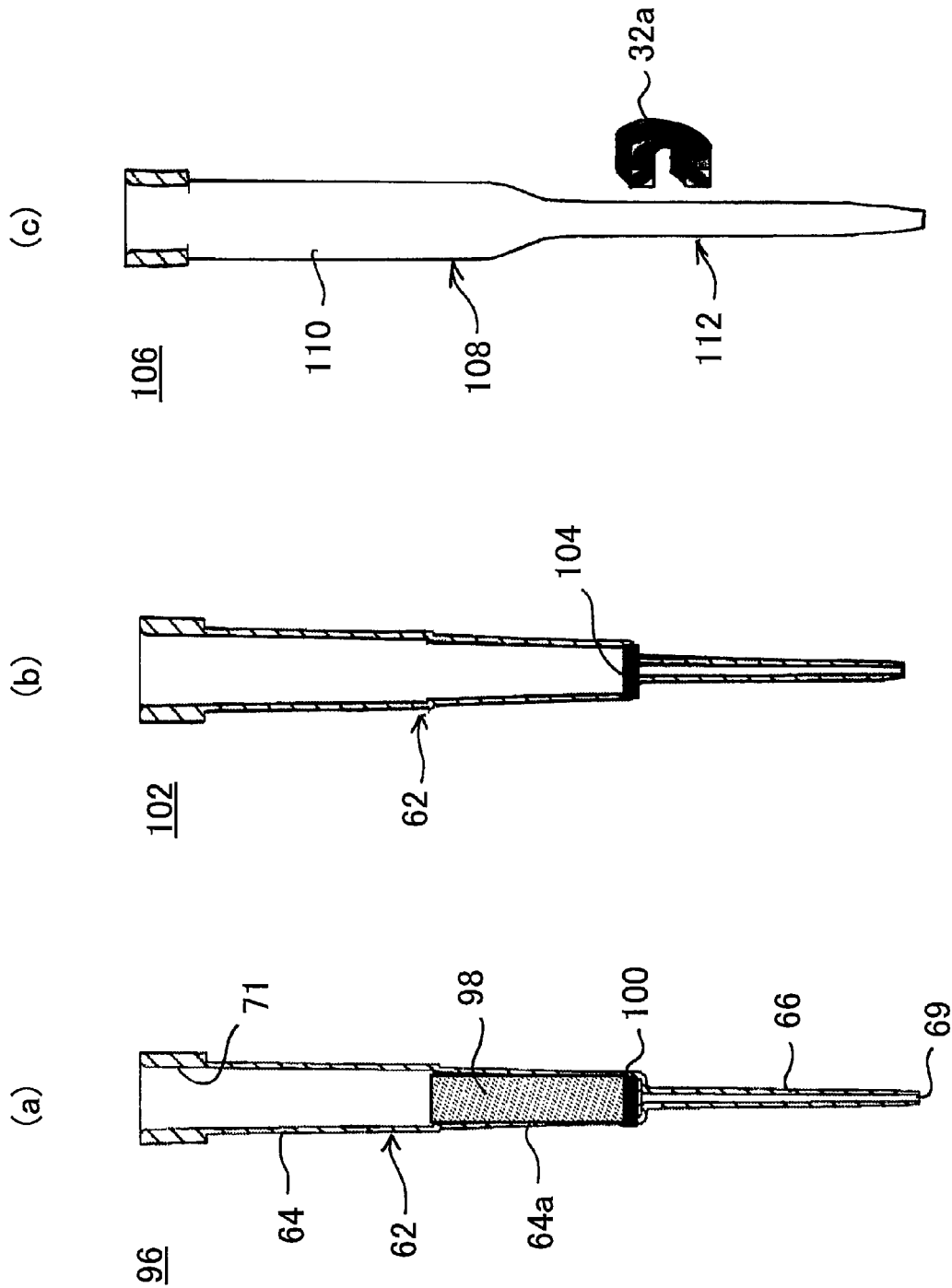
FIG. 8 shows other column tips of the invention.

FIG. 8 shows another column tip 96, filter tip 102 and dispensing tip 106, which can be fitted to the nozzle 14.

The column tip 96 is the tip-shaped vessel 62 enclosed with a gel for a gel filtration chromatography such as Sephadex or Sephacryl using a single filter 100. The filter tip 102 has a membrane filter or a ultrafiltration membrane enclosed as a filter 104. With pressurizing from the top or natural pressurizing, elution can occur. When using an agarose gel to fractionate proteins based on the size, it is effective for increasing the accuracy to have a longer valid column length to enclose the packing.

The controlling part is discussed here.

This controlling part controls the suction and discharge mechanism 16 and the moving means (not shown) with regard to quantities, pressure, flow rate, the number of cycles, time or position of the suction and discharge by the nozzle 14 based on a structural requirement relating to the structure of the one or more types of column tips 12, 78, 82, and 96 to be fitted to the nozzle 14 and a processing requirement relating to the processing contents involving one or more types of subject fluids subjected to the suction and discharge of the column tips. The structural requirement includes a plurality of items relating to the structure of the tip-shaped vessel 62 of the column tip, the structure of the filters 65, 67 or the morphology, and nature of the packing enclosed, and the processing requirement includes a plurality of items relating to the processing contents including each housing position, type, nature or quantity of one or more types of the subject fluids subjected to the suction and discharge of the column tips.

The controlling part has an operation panel 24 and a lid-fitted IC card insertion port 30 as a designating part for designating the column tips and the processing using this column tip, a requirement generating part which generates a structural requirement relating to the designated column tips and a processing requirement relating to the designated processing, and an optimum parameter determining part which determines, based on the generated the structural requirement and processing requirement, an optimum parameter with which the suction and discharge mechanism and the moving means should be in accordance. The requirement generating part and the optimum parameter determining part are provided in the information processing device. This information processing device has a CPU, memories, software stored in a memory for controlling, which are not shown in the figures.

Figure 9:
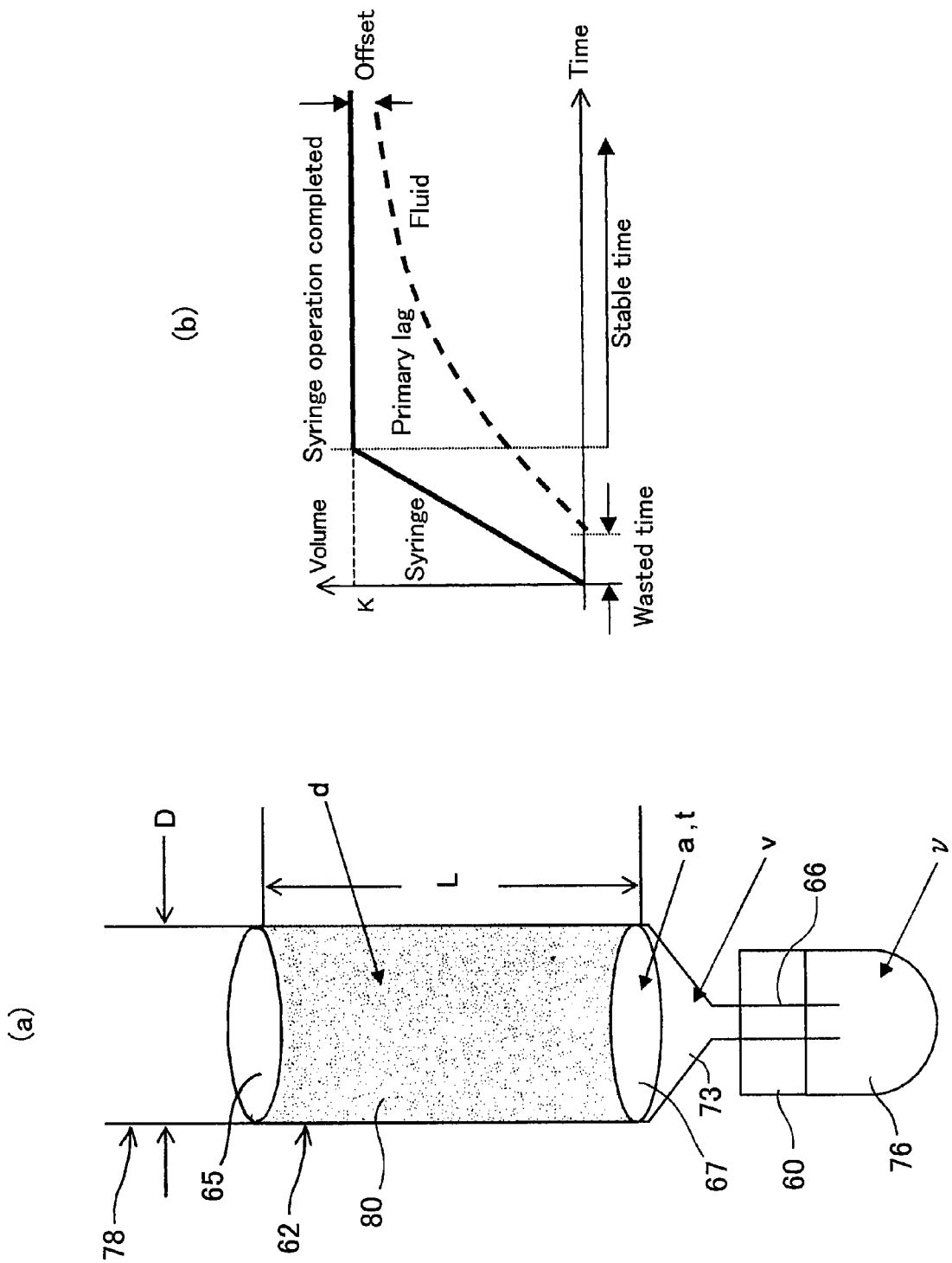
FIG. 9 is a schematic view of an optimum parameter determining part of a controlling part according to the second embodiment of the invention.

Based on FIG. 9, an example that an optimum parameter determining part determines the optimum parameter based on the structural requirement and processing requirement generated by the requirement generating part is described specifically below.

To determine these optimum parameter based on the structural requirement and processing requirement generated by the requirement generating part of the controlling part, various factors serving as a resistance against suction and discharge of a fluid, such as a packing 80, supporting filter 67, 65 and the like, all provided in the column tip 78, should be taken into account.

FIG. 9(a) is a schematic view near the valid column region of the column tip 78. Based on FIG. 9(a), examples of the structural requirement and the processing requirement generated by the requirement generating part are shown below.

Among the structural requirement, one relating to the structure of the tip-shaped vessel 62 includes the column's inner diameter D, which is 5.1 mm in this case, the valid column length L (excluding a filter part), which is 2.5 mm in this case, the dead volume v corresponding to the capacity of the tube having a small diameter 66 and the transfer part 73, which are not involved in the reaction which is 50µ liters. One relating to the structure of the filters 67 and 65 includes the filter thickness t, which is 1.4 mm in this case and the porosity a of the filter 67. While the pore size of the filters 67 and 65 in this case is 80 to 120 µm (POREX, Hydrophobic), a particle smaller than the pore size can be retained due to its substantial thickness. One relating to the morphology of the packing 80 in this case includes the particulate form, its mean particle size d, which is 90 µm in this case, while one relating to the type and the nature includes, for example, the type, NI Sepharose (GE Healthcare Bioscience, NI Sepharose 6 Fast Flow). The processing requirement includes the type of the subject fluid which is a suspension of His-Tag-GFP as a biological substance, the concentration which is 600µ gram/600µ liters, and the quantity which is 650 µL. The quantity of the subject fluid is 600µ liters. As processing contents, those included are the case corresponding the adsorption of the subject fluid in Step S2 shown in FIG. 10, where the biological substance described below is brought into contact with the packing 80 to effect a binding reaction movement.

The optimum parameter determining part determines the optimum parameters based on the structural requirement and the processing requirement as detailed above.

For determining the optimum parameters, it is a concern that a fluid resistance of the column tip 78 occurres for the respective factors. The fluid resistance of the column tip 78 is mostly the sum of the resistance by the filter and the resistance by the packing. The resistance by the packing is inversely proportional to the square of the ratio to the standard inner diameter D, proportional to the standard valid column length L, and proportional to the viscosity v of the subject fluid. On the other hand, the resistance by the filter is inversely proportional to the square of the ratio to the standard inner diameter D, proportional to the ratio to the standard filter thickness, proportional to the ratio to the standard porosity, and proportional to the viscosity v of the subject fluid. In addition, there is a dependence also on the processing contents of the processing requirement.

On the other hand, there is a time lag between the cylinder operation (solid line) and the fluid response (dotted line) as shown in FIG. 9(b) as a result of taking the fluid resistance into account. Such a difference is considered to be due mainly to the fluid resistance, in view of the understanding that there will be no time lag when suctioning and discharging an ideal fluid against zero resistance.

Thus, between the cylinder operation and the fluid response, there is a time lag of a "wasted time" corresponding to the difference in the time between the suction and discharge operation starting time for the suction and discharge mechanism and the fluid movement starting time for column tips, and the fluid does not enter the column tip immediately after the operation of the cylinder. In addition, in contrast to a linear increase in the capacity of the cylinder due to the cylinder operation, the fluid entry exhibits an asymptotic increase, thus posing a primary lag. Moreover, the suction quantity does not become identical completely even after a sufficient time elapsed after cylinder operation, thus posing an offset. This is applicable also to the response upon the fluid discharge.

Accordingly, the optimum parameter determining part determines, based on the response property of the fluid which is suctioned into or discharged from the column tip, the optimum parameters when taking the resistance into consideration based on this FIG. 9(b). Thus, by defining a suction corrected quantity or a discharge corrected quantity involving the offset fluid quantity as an optimum parameter for a desired suction quantity or discharge quantity, the influence by the offset can be reduced, and when the resistance in the column tip is high then the determination is made so that the wasted time and the primary lag are reduced by suctioning slowly. In addition, by defining the time until stability after the fluid is suctioned into or discharged from the column after completion of the cylinder operation as "waiting time after suction" and "waiting time after discharge", the starting time for the next operation is determined as an optimum parameter.

The optimum parameter includes a "stirring volume". The stirring volume may vary depending on the quantity of a test sample. Depending on the proportion between the packing volume and the valid column region capacity, the quantity of the liquid capable of being suctioned may vary. When the packing volume is enclosed at 100% in the valid column region, the subject fluid can be introduced in a stirring volume exceeding this valid column region, but at a lower % it should be required that the stirring volume of the subject fluid is determined to be a value not exceeding the valid column region capacity for the purpose of preventing air from coming into.

In this manner, while for each structural requirement and processing requirement the respective optimum parameters should be determined, such a case-by-case determination of the optimum parameters is quite tiresome. Accordingly, in this embodiment, from standard structural requirement and processing requirement, standard optimum parameters are determined preliminarily, and in other cases the optimum parameters are estimated based on the ratio to or difference from the standard factors.

Accordingly, the optimum parameter determining part determines the optimum parameters using the column tip 78 shown in FIG. 9(a) as a standard. In such a case, the standard optimum parameters are determined for the stirring volume to be 800µ liter in this case, for the stirring cycle to be 10 times in this case, for the suction flow rate to be 70µ liter/second in this case, for the waiting time after suction to be 5 seconds in this case, for the discharge flow rate to be 70µ liter/second in this case, for the waiting time after discharge to be 5 seconds in this case. The suction flow rate and the discharge flow rate here are cylinder-driven flow rates and are not the flow rates of the fluid suctioned or discharged actually.

Otherwise, respective optimum parameters are calculated considering the ratio to the standard value to the inner diameter of the resistance of the packing, the ratio to the standard value for the valid column length, and the ratio to the particle size, the optimum parameters are changed considering their tendencies.

Figure 10:
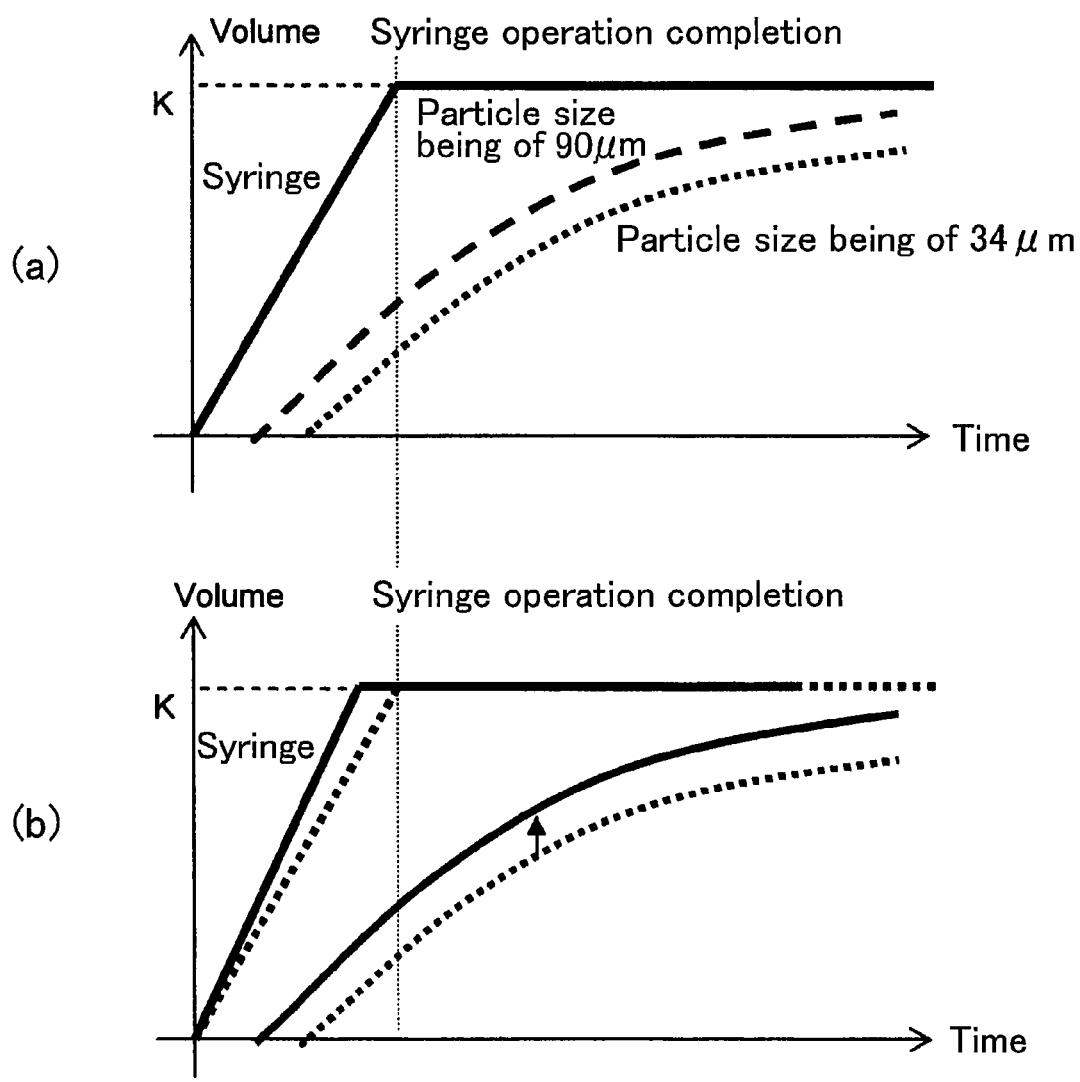
FIG. 10 is a schematic view of an optimum parameter determining part of a controlling part according to the second embodiment of the invention.

FIG. 10 shows an example of the determination of the optimum parameters other than the standard optimum parameters.

FIG. 10(a) indicates that when compared to the response of a fluid to the packing 68 having a standard particle size d of 90 µm (long-dotted line) one having the particle size d of 34 µm (otherwise identical factors) leads to a higher plugging density which leads to a higher resistance, resulting in an increase in the "wasted time", as well as a further increase in the primary lag, and also an increase in the offset level. Accordingly, as shown in FIG. 10(b), in order to achieve, even when the particle size is 34 µm, the flow rate of the fluid when the particle size is 90 µm, the cylinder operation rate should be increase. Therefore, in this case, the optimum parameters are determined to effect either or all of the followings: (1) the waiting time after suction and discharge is prolonged; (2) The stirring volume is increased; (3) For achieving an actual suction and discharge flow rate of the fluid which is identical to that with the mean particle size of 90 µm, the suction and discharge flow rate is set at a higher rate.

Figure 11:
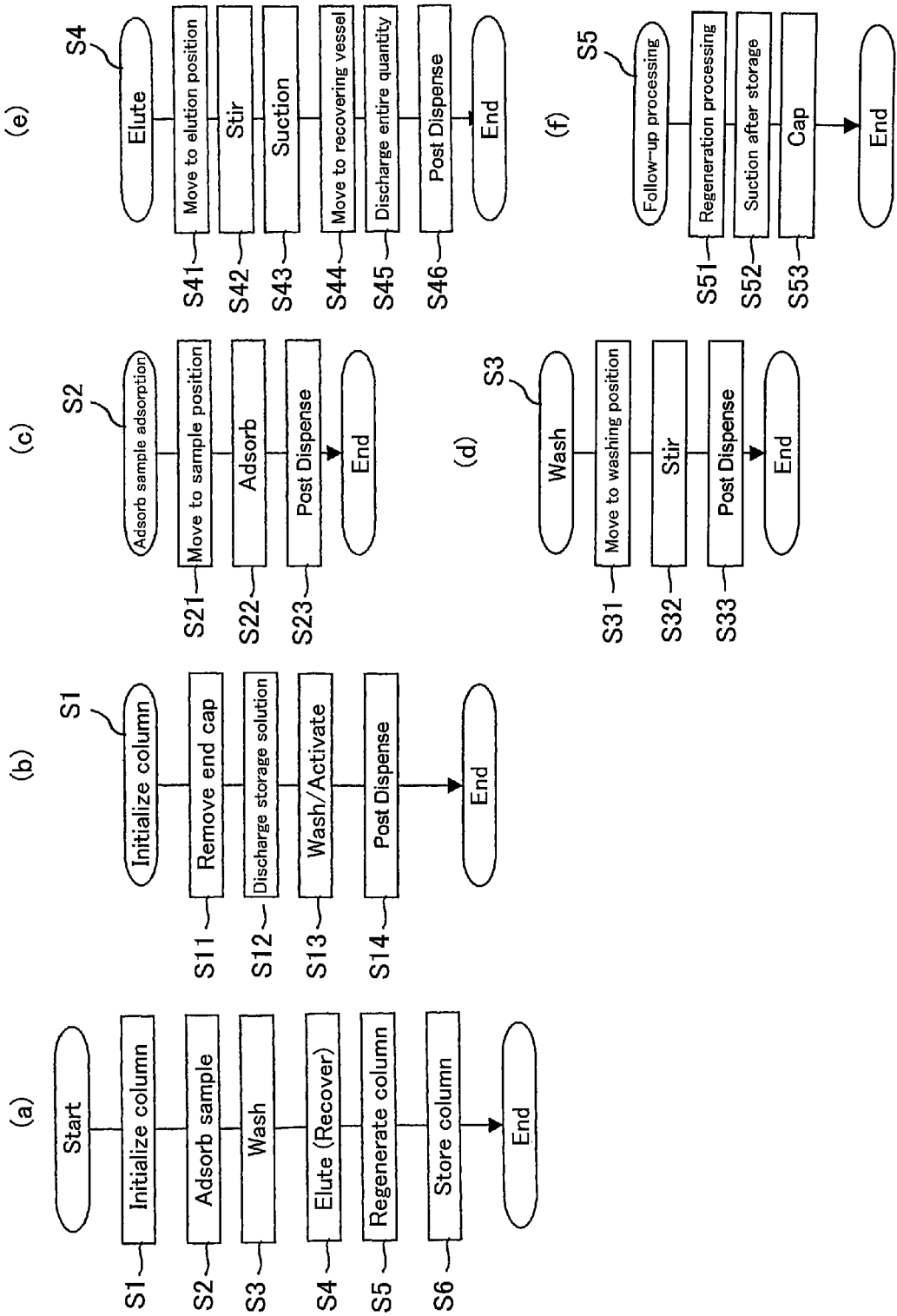
FIG. 11 is a flow chart indicating a column tip processing according to a fourth embodiment of the invention.

Based on FIG. 11, a column tip processing method according to the fourth embodiment of the invention is described.

To process a column tip, first, in Step S1, the column tip 78 is initialized. Upon initialization of the column tip 12, the column tip 12 employed and the processing thereof are designated from the operation panel 24 and the lid-fitted IC card insertion port 30 as the designating part. Thus, the number of test samples to be processed, the quantity of the test sample liquid, the positions where the test samples are placed, the processing protocol, the column regeneration processing if any are entered. The processing protocol includes the details of the processing contents as well as the control parameter set thereof.

T Step S1 column initialization step involves, as a preliminary procedure, removal of the upper lid of the column tip 12 shown in FIG. 4 while housing 12 tips in the 12 tip housing parts 61 in a tip rack 18 of the housing part group 20. The nozzle head 15 is moved relatively in the direction of the X axis to this tip housing part 61, this nozzle head 15 is lowered in the direction of the Z axis, and the nozzles 14 are inserted and put all at once to the opening 71 for fitting, whereby fitting 12 column tips 12 to the nozzle head 15.

Subsequently in Step S11, the nozzle head 15 is raised in the direction of the Z axis, the column tips 12 are moved along the direction of the X axis, and the cap 72 is allowed to be placed under the detaching plate 42 in this tip rack, whereby inserting so that the tube having a small diameter 66 reaches the holes 59a. Then, the nozzle head 15 is raised in the direction of the Z axis to drawn the cap 72 down apart.

In Step S12, the activation maintaining fluid housed in the column tips 12 is allowed to be discharged into a waste tank (not shown), and then in Step S13 the X axis moving body 94 is moved along the direction of the X axis, whereby moving the nozzle head 15 relatively to the reagent rack 55 as the fluid housing part group. Then, after washing and activation are effected, the processing for conditioning the packing is conducted. This is accomplished in such a manner that a certain buffer solution as a subject fluid is suctioned a discharged repetitively (equilibration). In such a case, as suction and discharge parameters, the buffer position, the suction position, the stirring fluid volume, the number of stirring cycles, the suction flow rate, the halting time after suction, the discharge flow rate, and the halting time after discharge are determined.

In Step S14, a discharge motion is effected for discharging the washing and activation fluid thoroughly from the column tips. In such a case, as parameters, the height which prevents the washing or activation fluid from being brought into contact with the outside of the tip as far as possible, the start waiting time, the discharge quantity, the discharge flow rate are determined.

The sample adsorption step in Step S2 involves Step S21 in which the nozzle head 15 is moved to the position of the sample tube 60 on the stage 13 on which the sample as a subject fluid is housed, whereupon inserting the hollow end 69 of the column tip 12 into this sample tube 60. In Step S22, by repeating suction and discharge, the packing and the subject fluid are brought into contact with each other, whereby allowing the biological substance to be adsorbed onto the packing. Upon this, the controlling part determines the optimum parameters as mentioned above, and then, based on these optimum parameters, controls the suction and discharge mechanism and the moving means.

As suction and discharge parameters, "stirring volume", "the number of stirring cycles and time period", "suction flow rate", "halting time after suction", "discharge flow rate", "halting time after discharge" are exemplified. For these parameters, the optimum parameters are determined taking the followings into consideration. The "stirring volume" is varied depending on the quantity of a test sample. Depending on the packing and the tip capacity encompassed by the structural requirement, the quantity of the fluid capable of being suctioned may vary. With regard to the "number of stirring cycles and time period", repetitive passage through the packing is required when the ability of binding to the ligand is poor. A prolonged contact time period is required. With regard to the "suction flow rate", there is a risk of pealing off unless the suction is slow enough when the ability of binding to the ligand is poor. When the ability of binding is sufficient, it may sometimes be efficient to effect a rapid suction whereby establishing the suspending state of the packing. The "halting time after suction" is a time period during which the complete immersion of the packing in a test sample solution as a subject fluid is maintained. Since the flow resistance becomes higher when the packing is too dense or the packing retaining mesh is too fine, the fluid may sometimes not be suctioned completely unless a sufficient halting time is provided. With regard to the "discharge flow rate", there is a risk of pealing off unless the discharge is slow enough when the ability of binding to the ligand is poor. With regard to the "halting time after discharge", since the flow resistance becomes higher when the packing is too dense or the packing retaining mesh is too fine, the fluid may sometimes not be suctioned completely unless a sufficient halting time is provided.

In Step S23, a processing is conducted for preventing any carryover of unnecessary contaminants into the subsequent processing. Required parameters include "discharge height", "waiting time for discharge", "discharge quantity", "discharge flow rate", for which optimum parameters are determined taking the followings into account. The "discharge height" is a height which prevents the sample solution as a subject fluid from being brought into contact with the outside of the tip as far as possible. A height preventing any droplet from being formed on the end when the tip is raised after the fluid discharged from the tip again is brought into contact with the sample fluid as a subject fluid is designated. The "waiting time for discharge" designates a time period until the unnecessary subject fluid present inside and outside of the tip drops down spontaneously to the lower end of the tip. The "discharge quantity" designates a quantity for complete discharge of the unnecessary fluid retained in the end of the tip. The "discharge flow rate" designates a flow rate for complete discharge of the unnecessary fluid retained in the end of the tip.

Step S3 shows a washing step, including Step S31 for movement to the washing position and Step S32 for stirring by allowing the washing fluid as a subject fluid to be suctioned into and discharged from the column tip 12 repetitively. As parameters in the washing step, those occurring by replacing the subject fluid from the sample in the sample adsorption step mentioned above into the washing solution are employed. Step S33 is a processing for preventing any carryover of unnecessary washing fluid into the subsequent processing, and its parameters are those occurring by replacing the subject fluid in the parameters in Step S23 in the sample adsorption step mentioned above from the sample into the washing solution. The washing step can be conducted repetitively until a sufficient washing is achieved in a plurality of the fluid housing parts or in the fluid housing parts of different washing fluids.

Step S4 shows an eluting step, including Step S41 for movement to the position which is the suction and discharge position as a parameter and where an eluted fluid is housed. The position where the eluted fluid is housed is designated by ligand and the sample of the subject fluid. In Step S42, the column tip 12 is subjected to a repetitive suction and discharge of the eluted fluid. When conducting concentration, the eluted fluid may not discharge into the column sufficiently. In such a case, the stirring fluid quantity should be adjusted so that the eluted fluid is suctioned to the position allowing all of the packing is passed through.

In Step S43, the entire quantity of the eluted fluid is suctioned. Accordingly, as a suction quantity, the parameters are adjusted so that an extra quantity in addition to the quantity of the eluted fluid is suctioned.

In Step S44, the nozzle head 15 is moved relatively to the recovery vessel position. Step S45 serves to discharge the entire quantity. Step S46 serves to discharge an extra quantity in addition to the eluted fluid flowing quantity, since the eluted fluid tends to remain in the column tip 12. Before conducting the extra discharge, a waiting time for the fluid in the column tip 12 to drip down to the end of the tip is provided.

Step S5 is a follow-up processing. This step conducts a processing for a future use when a used column tip 12 can be used again.

Step S51 conducts a regenerating processing. The regenerating processing conducts the packing washing and the suction and discharge of the regenerating fluid for establishing a state suitable for the storage. Accordingly, stirring quantity, the number of stirring cycles, stirring rate are selected. In Step S52, a storage fluid or an activation maintaining fluid is suctioned. The suction of the storage fluid serves to fill the storage fluid for preventing the packing in the column from being dried or fungal organisms from being allowed to grow.

In Step S53, for removing the column tip 12 from the nozzle 14 while allowing the storage fluid to remain still as being filled, the end is fitted with a cap. In the case of a high throughput system, the fitting is accomplished automatically. In the case of a compact-type system for a small number of samples, the fitting may be accomplished manually through a user interface.

Figure 12:
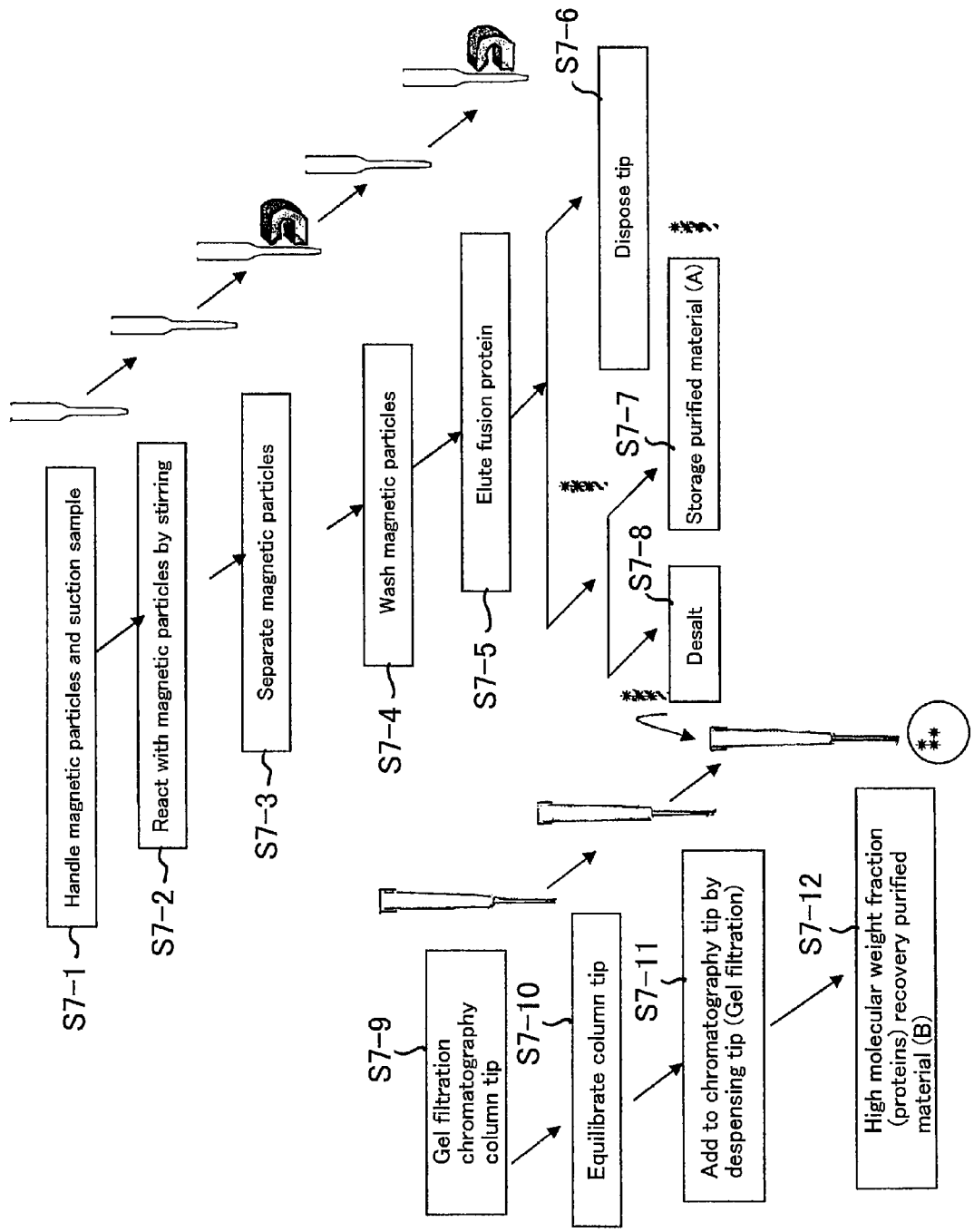
FIG. 12 is a flow chart of a column tip processing according to a fifth embodiment of the invention.
Figure 13:
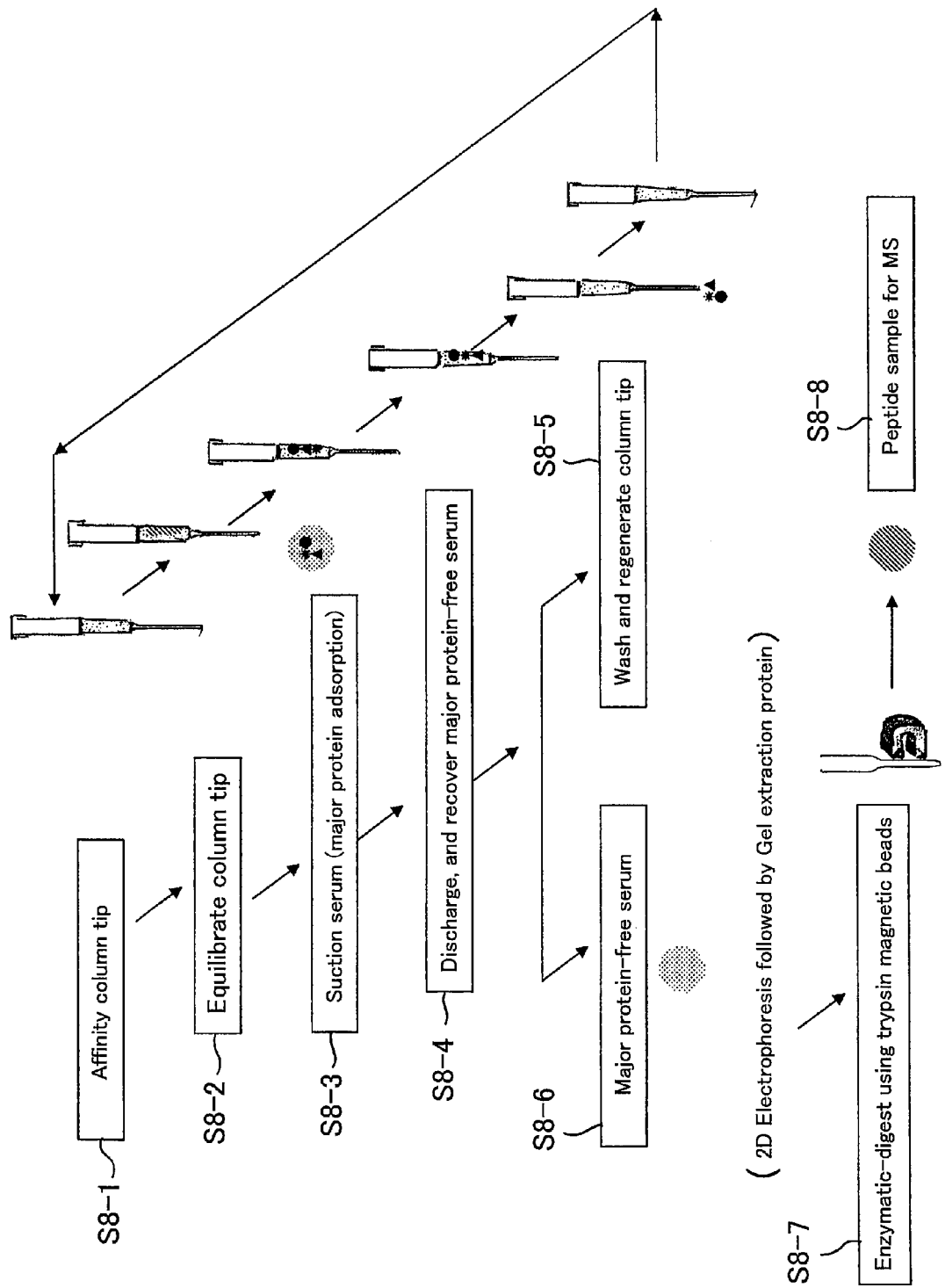
FIG. 13 is a flow chart of a column tip processing according to a sixth embodiment of the invention.
Figure 14:
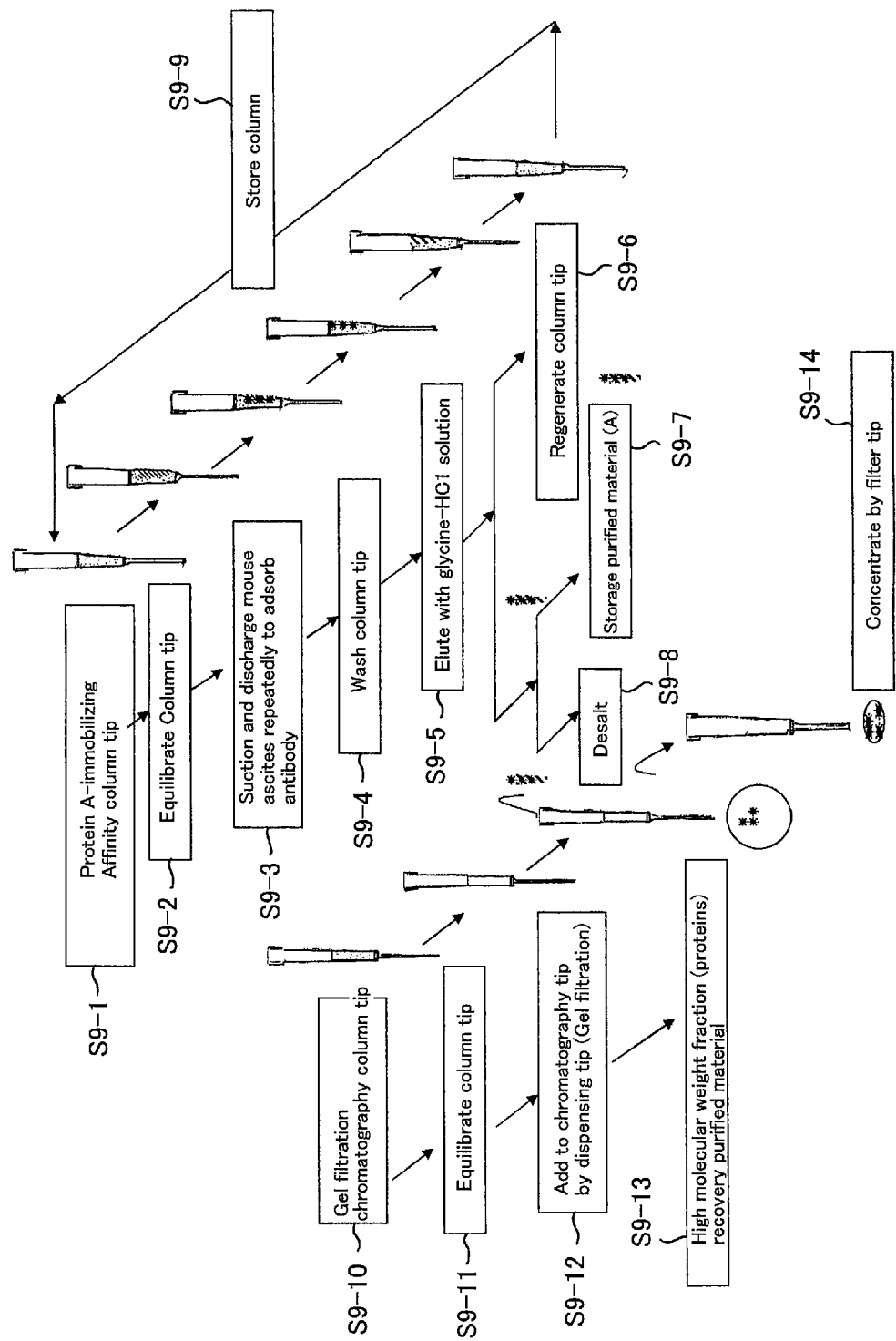
FIG. 14 is a flow chart of a column tip processing according to a seventh embodiment of the invention.

FIGS. 12 to 14 show specific processings (processings according to the fourth embodiment to the sixth embodiment) with regard to any combination of one or more types of column tips, filter tips or dispensing tips (at least one type of columns should be included).

FIG. 12 shows an example of a recombinant protein purification processing, including a magnetic particle-based fusion protein purification using the dispensing tips and a protein analysis pretreatment using gel filtration column tips. In Steps S7-1 and S7-2, the dispensing tips 106 are fitted to the nozzles 14 of the nozzle head 15, and then, using these dispensing tips 106, a subject fluid containing a GST fusion protein or histidine-tagged fusion protein and a magnetic particle suspension having an anti-GST antibody or glutathione and a nickel ion immobilized thereon are reacted with each other by stirring.

Step S7-3 serves to use a magnetic means 32 provided in the nozzle head to allow the magnetic particles to be adsorbed onto the inner wall of the dispensing tip 106 whereby accomplishing separation. Step S7-4 serves to wash with a washing fluid. Step S7-5 serves to elute the fusion protein from the magnetic particles using a salt solution at a high concentration or a solution of a reduced form of glutathione in the case of the GST fusion protein and an imidazole solution in the case of the histidine-tagged fusion protein, followed by housing in tubes or the like on the stage 13.

Then, in Step S7-6 the dispensing tips are detached from the nozzle 14. Then, in Step S7-9, the gel filtration column tips 96 such as of Sephadex or Sephacryl are housed in the housing part group 20. In Step S7-10, the column tips 96 are made free of the storage fluid for maintaining activation, and equilibrated. In Step S7-11, the dispensing tips are used to add the eluted fluid to these gel filtration column tips 96, and then, after connection to the nozzles 14 of the nozzle head 15, a high molecular weight fractionation (protein) is conducted in Step S7-12 to recover the proteins sequentially in the order of higher molecular weights, followed by desalting or removal of low molecular weight contaminants, whereby accomplishing purification.

FIG. 13 shows an example of a processing for removing major proteins in a serum, which employs an affinity column tip in combination with a dispensing tip.

In Step S8-1, the column tips 78 each enclosed with an affinity gel having antibodies (several types) specific to the major proteins immobilized thereon are used as being fitted to the nozzles 14. In Step S8-2, the column tips are equilibrated. In Step S8-3, the serum is suctioned and discharged to allow the major proteins to be adsorbed. In Step S8-4, a serum now free of the major proteins is discharged.

A protein extracted by a two dimensional electrophoresis is subjected to Step S8-7 where after the column tips are detached and then the dispensing tips are fitted, and the trypsin enzyme bound to the magnetic particles is used to effect an enzymatic digestion, followed by using the magnetic force means to allow the magnetic particles to be adsorbed onto the inner wall of these dispensing tips whereby effecting separation, followed by Step S8-8 where a peptide sample for a mass spectrometry is obtained.

FIG. 14 shows an example of an antibody purification processing, especially a pretreatment of a protein analysis sample using an affinity column tip, a gel filtration column tip, and a filter tip.

In Step S9-1, a column tip 78 enclosed with an affinity gel such as Protein A or Protein G is fitted to the nozzle 14. In Step S9-2, this column tip 78 is equilibrated. In Step S9-3, a mouse ascites is suctioned and discharged repetitively to allow the antibody to be adsorbed. In Step S9-4, the column tip 78 is washed. In Step S9-5, the antibody adsorbed onto the packing is eluted with a glycine HCl buffer solution. The eluted fluid is discharged to and housed in an appropriate fluid housing part in the housing part group 20.

After detaching the column tip 78 from the nozzle 14 of the nozzle head 15, the column tip 96 for the gel filtration is housed in the tip rack in the housing part group 20 in Step S9-10. In Step S9-11, the column tip 96 for the gel filtration is equilibrated. In Step S9-12, the dispensing tip is fitted to the nozzle head and the fluid eluted from the opening 71 for fitting is added to the column tip 96 for the gel filtration. After detaching the dispensing tip from the nozzle 14 of the nozzle head 15, the column tip 96 for this gel filtration is fitted to each nozzle 14 of the nozzle head 15, and then discharge in Step S9-13 followed by a high molecular weight fractionation results in recovery and purification of the protein.

In Step S9-14, after detaching the column tip 96 from the nozzle 14, the product is inserted to a filter tip 102 housed in the housing part of the stage 13, and then discharged and concentrated by fitting this filter tip 102 to the nozzle 14 followed by applying a pressure by the suction and discharge mechanism.

Figure 15:
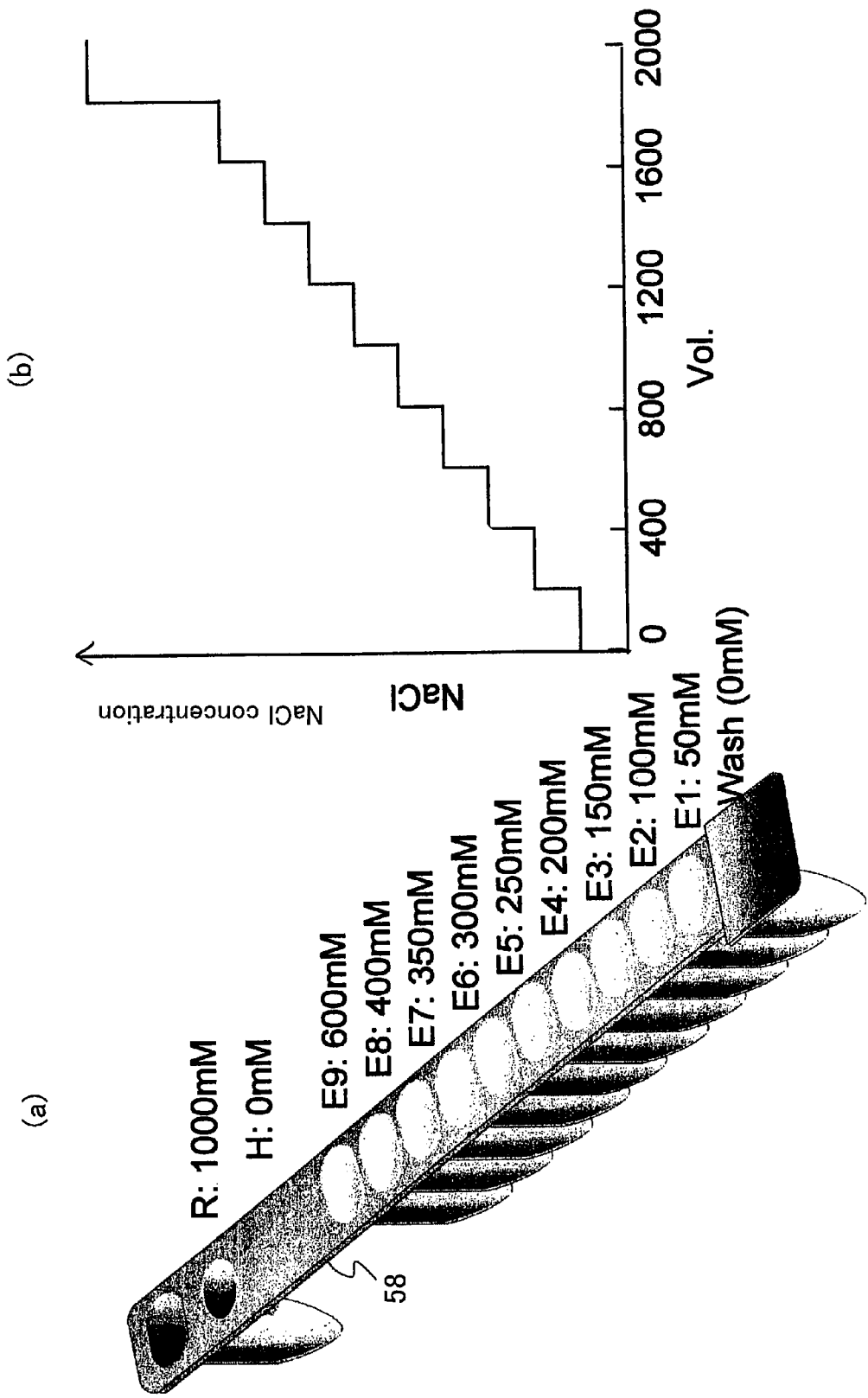
FIG. 15 shows a view of a fluid housing part group according to an eighth embodiment of the invention as well as the concentrations of the fluids to be housed.

FIG. 15 shows a buffer solution as a subject fluid employed when conducting elution of an intended biological substance adsorbed in a column tip processing device 10 according to the 8th embodiment of the invention.

In this embodiment, a column tip 78 is employed, and as a packing a substance employed in an affinity chromatography or an ion exchange chromatography may for example be enclosed, and allowed to adsorb the intended protein, such as a bacteria-derived enzyme. In order to elute the adsorbed intended protein, buffer solutions having a certain difference from each other in the concentration of a salt along with the concentration gradient are housed in one reagent prepack cartridge 58 present on the state 13 of the column tip processing device 10. Here, the difference in the concentration of the salt is not necessarily constant. In this case, as shown in FIG. 15, those having the concentrations starting from 0 mM for washing and thereafter, by the difference in the concentration of 50 mM, from 50 mM to 400 mM (E1 to E8) and 600 mM (E9) are housed. These buffer solutions can be produced by mixing the buffer solution (R) at 1000 mM and the solution (H) at 0 mM housed similarly in this prepack using the dispensing tip fitted to the nozzle 14. For example, the buffer solution at 500 mM can readily be produced by mixing R with H each in 50 percents.

Each embodiment thus described is presented specifically for the purpose of a better understanding of the present invention, and is not intended to impose any restriction on other embodiments. Accordingly, variations can be made as far as the subject matter of the invention is not changed. For example, the embodiments of the invention described above can be applied to a processing in the field of genetics, although they are described mainly with regard only to proteins. For example, by combining a dispensing tip employing a magnetic particle with a gel filtration column tip, it is possible to conduct a nucleic acid extraction, a PCR product purification and capture of intended substances, as well as a concentrating processing. In addition, by combining a dispensing tip employing a magnetic particle with a filter tip, it is possible to conduct a nucleic acid extraction, a PCR product purification, concentration or a high purity purification (complete removal of a trace amount of magnetic particles).

Also in the field of proteins, otherwise by using a dispensing tip employing a magnetic particle and a filter tip, it can be used in a fusion protein extraction and purification, a molecular sieve (high molecular weight protein removal) processing. In addition, by using a dispensing tip employing a magnetic particle, a gel filtration column tip and a dispensing tip of another type, it can be used for removal of the major protein, for exchange of a buffer solution, and for an enzymatic digestion (trypsin-immobilizing magnetic particle) processing. In addition, by using an affinity column tip and a gel filtration column tip, it can be used in a processing for removing the major proteins and exchanging buffer solutions, or in a processing for affinity purification followed by buffer exchange. In addition, by using an affinity column tip, a gel filtration column tip and a filter tip, it can be used for removing the major proteins and exchanging buffer solutions, and then conducting a concentration processing. Moreover, by using an affinity column tip, a gel filtration column tip, a filter tip and a dispensing tip, it can be used in a major protein removing processing, a buffer exchange, concentration and enzymatic digestion processings.

INDUSTRIAL APPLICABILITY

The present invention relates to a column tip processing device and a column tip processing method. The invention relates to various fields requiring a handling of biological high molecular weight substances and biological low molecular weight substances including
genetics, immunology, amino acids, proteins, saccharides and the like, such as industrial fields, agricultural field including foods, agricultures, marine resource processings, pharmaceutical fields, medical fields including hygiene, welfare, immunology, disease, genetics and the like, chemical or biological or physical fields and the like. The invention is a method which is effective especially in a case where a large number of reagents or substances are employed in a series of processings which is conducted in a certain order continuously.

DESCRIPTION OF REFERENCE NUMERALS

10: Column tip processing device
12, 78, 82, 96: Column tip
14: Nozzle
15: Nozzle head
16: Suction and discharge mechanism
20: Housing part group
24: Control part

The invention claimed is:

1. A column tip processing device comprising:
a nozzle head having a single or multiple-channeled nozzle;
a suction and discharge mechanism conducting suction or discharge of a gas via the nozzle;
one or more types of column tips each having a tip-shaped vessel having a fitting opening to be fitted to the nozzle and a hollow end through which a fluid can flow in or out in response to the suction or discharge of the gas and a packing enclosed in the tip-shaped vessel;
a stage provided with a fluid housing part group including a plurality of fluid housing parts into each of which the hollow end can be inserted and which house or can house various solutions; and,
moving means for moving the nozzle head relatively to the fluid housing part group;
and also having a controlling part which controls the suction and discharge mechanism and the moving means with regard to quantities, pressure, flow rate, the number of cycles, time or position of the suction or discharge by the nozzle based on a structural requirement relating to the structure of the one or more types of column tips to be fitted to the nozzle and a processing requirement relating to the processing contents involving one or more types of subject fluids subjected to the suction or discharge of the column tips,
wherein the controlling part has a designating part which designates the column tips and a processing using the column tips, a requirement generating part which generates a structural requirement relating to the designated column tips and a processing requirement relating to the designated processing, and an optimum parameter determining part which determines, based on the generated structural requirement and processing requirement, an optimum parameter with which the suction and discharge mechanism and the moving means should be in accordance,
wherein the optimum parameter determining part determines an optimum parameter relating to suction or discharge, based on the generated corresponding structural requirement and processing requirement for each of the column tips and processing contents, in order to reduce the difference in time between the suction or discharge operation starting time for the suction and discharge mechanism and the fluid movement starting time for column tips and also the offset of suction or discharge operation quantity and the suction or discharge quantity of the fluid for the column tip after achieving the operation quantity.

2. The column tip processing device according to claim 1, wherein the packing is enclosed in the tip-shaped vessel using at least one filter provided in a manner to partition the tip-shaped vessel,
the structural requirement includes a plurality of items relating to the structure of the tip-shaped vessel, the structure of the filter or the morphology, type and nature of the packing enclosed, and
the processing requirement includes a plurality of items relating to the processing contents including each housing position, type, nature or quantity of one or more types of the subject fluids subjected to the suction or discharge of the column tips.

3. The column tip processing device according to claim 1, wherein the optimum parameter determining means determines, based on a standard structural requirement which sets predetermined one or two standard column tips and at least a part of the plurality of the items of the structural requirement corresponding to the standard processing contents at one or more standard values and a standard processing requirement which sets at least a part of the plurality of the items of the processing requirement at one or more standard values, an optimum parameter corresponding to structural requirements and processing requirements other than the standard structural requirements and the standard processing requirement.

4. The column tip processing device according to claim 1, wherein the stage has a temperature raising and lowering vessel which raises or lowers the temperature in response to an external signal, at least one of the fluid housing part is housed in the temperature raising and lowering vessel, and the control of the temperature of the subject fluid is conducted on the moving means based on the processing requirement.

5. The column tip processing device according to claim 1, wherein on the stage one or more said column tips, one filter tip having a fitting opening to be fitted to a nozzle, or one dispensing tip, and a detaching part for detaching the column tip, filter tip or dispensing tip fitted to the nozzle are provided,
the controlling part conducts, on the suction and discharge mechanism and the moving means, the control of the fitting and detachment of the column tip, filter tip or dispensing tip based on the structural requirement and the processing requirement.

6. The column tip processing device according to claim 1, wherein at least a part of the fluid housing part group is provided with a piercable thin film covering the opening of the fluid housing part,
the nozzle head is provided with a piercing pin capable of piercing the thin film, and
the control of the thin film piercing is conducted on the moving means based on the processing requirement.

7. The column tip processing device according to claim 1, wherein the nozzle head is provided with a fall off preventing part which prevents the fall off from the nozzle by engaging with the tip-shaped vessel of the column tip fitted to the nozzle, and
the control of the fall off prevention and a cancellation thereof by the fall off preventing part is conducted on the moving means based on the structural requirement and the processing requirement.

8. A column tip processing method comprising:
   based on a structural requirement of one or more types of column tips each having a tip-shaped vessel having a fitting opening conducting suction or discharge of a gas by a suction and discharge mechanism and a hollow end through which a fluid can flow in or out in response to the suction or discharge of the gas and a packing enclosed in the tip-shaped vessel, and a processing requirement relating to the processing contents involving one or more types of subject fluids subjected to the suction or discharge of the column tips,
   a fitting step for fitting a column tip to the nozzle at the fitting opening by moving the nozzle relatively between it and the housing parts of the column tip housed therein;
   a contacting step for inserting the hollow end into the fluid housing part by a relative movement between one or more fluid housing part housing the subject fluid and the nozzle whereby suctioning and discharging the subject fluid according to quantities, pressure, flow rate, the number of cycles, time or position of the suction or discharge by the nozzle determined based on the requirement, whereby bringing the packing into contact with the subject fluid;
   a discharging step for discharging the subject fluid from the column tip into one or more the fluid housing parts;
   a designating step for designating column tips to be fitted and processing contents to be processed; and,
   a generating step for generating a structural requirement corresponding to the column tips designated and generating a processing requirement corresponding to the processing contents designated;
   wherein the contacting step has an optimum parameter determining step for determining an optimum parameter based on the generated structural requirement and processing requirement, and a contact executing step for moving the nozzle while executing suction or discharge,
   wherein the optimum parameter determining step determines suction or discharge parameters, based on the generated corresponding structural requirement and processing requirement for each of the column tips and processing contents, while considering the difference in time between the suction or discharge operation starting time for the suction and discharge mechanism and the fluid movement starting time for column tips, the offset of suction or discharge operation quantity and the suction or discharge quantity of the fluid for the column tip after achieving the operation quantity, and the details of the reaction of the packing with substances contained in the subject fluid, in order to correct the difference between the targeted suction or discharge quantity at the completion of the suction or discharge and the suction or discharge quantity of the fluid for the column tip after completion of the operation.

9. The column tip processing method according to claim 8, further comprising a detachment step for detaching the column tips fitted to the nozzle, wherein the detaching step is conducted by means of a relative movement between the detaching part provided on the stage and the nozzle based on the structural requirement and processing requirement.

10. The column tip processing method according to claim 8, wherein, after the detaching step, fitting of at least one said column tip of another type, one filter tip connectable to the nozzle, or a dispensing tip housed on the stage is conducted, based on the structural requirement and processing requirement, by means of a relative movement between the nozzle and the housing part in which the column tip, filter tip or dispensing tip is housed.

11. The column tip processing method according to claim 8, wherein the packing is enclosed in the tip-shaped vessel using at least one filter provided in a manner to partition the tip-shaped vessel, the structural requirement includes a plurality of items relating to the structure of the member or the tip-shaped vessel fitted to the nozzle, the structure of the filter or the morphology, type and nature of the packing enclosed, and the processing requirement includes a plurality of items relating to the processing contents including each housing position, type, nature or quantity of one or more types of the subject fluids subjected to the suction or discharge of the column tips.

12. The column tip processing method according to claim 11, wherein, in the contact step, a temperature raising and lowering step for raising and lowering the temperature of the subject fluid based on the processing requirement is provided, and the raising and lowering of the temperature is conducted by means of a relative movement between the nozzle and the temperature raising and lowering vessel provided on the stage.

13. The column tip processing method according claim 8, wherein the optimum parameter determining step determines, based on a standard structural requirement for which one or more standard values are set for at least a part of the plurality of the items of the structural requirement generated corresponding to the predetermined standard column tips and the standard processing contents and a standard processing requirement for which one or more standard values are set for at least a part of the plurality of the items of the processing requirement, an optimum parameter corresponding to structural requirements and processing requirements other than the standard structural requirements and the standard processing requirement for those other than the predetermined standard column tips and processing contents.

14. The column tip processing method according to claim 13, wherein, in the contact step, a temperature raising and lowering step for raising and lowering the temperature of the subject fluid based on the processing requirement is provided, and the raising and lowering of the temperature is conducted by means of a relative movement between the nozzle and the temperature raising and lowering vessel provided on the stage.

15. The column tip processing method according to claim 8, comprising, after the discharge step,
   a step for washing the packing enclosed in the column tip by allowing a washing fluid as a subject fluid to be suctioned into and discharged from the column tip and
   an elution step for introducing an eluent into the column tip whereby eluting the processing subject fluid-carried biological substances which were adsorbed to, captured by and reacted with or bound to the packing.

16. The column tip processing method according to claim 15, wherein, in the contact step, a temperature raising and lowering step for raising and lowering the temperature of the subject fluid based on the processing requirement is provided, and the raising and lowering of the temperature is conducted by means of a relative movement between the nozzle and the temperature raising and lowering vessel provided on the stage.

17. An optimum parameter generating program stored on a non-transitory computer readable medium, for a column tip processing device comprising:
   a nozzle head having a single or multiple-channeled nozzle;
   a suction and discharge mechanism conducting suction or discharge of a gas via the nozzle;

one or more types of column tips each having a tip-shaped vessel having a fitting opening to be fitted to the nozzle and a hollow end through which a fluid can flow in or out in response to the suction or discharge of the gas and a packing enclosed in the tip-shaped vessel;

a stage provided with a fluid housing part group into which the hollow end can be inserted and which houses or can house various solutions; and, moving means for moving the nozzle head relatively to the fluid housing part group, wherein the optimum parameter generating program incorporates one or more column tips fitted to the nozzle and a designating data which designates the processing conducted using the column tips, generates, based on the designating data, a structural requirement data relating to corresponding column tip structure and a processing requirement data relating to the processing contents involving one or more types of subject fluids subjected to the suction or discharge of the column tips included in corresponding processing, and determines, based on the requirements generated, optimum parameter data prescribing quantities, pressure, flow rate, the number of cycles, time or position of the suction or discharge by the nozzle for the suction and discharge mechanism and the moving means, wherein the optimum parameter decision determines an optimum parameter data relating to suction or discharge, based on the generated corresponding structural requirement data and processing requirement data for each of the column tips and processing contents, while considering the difference in time between the suction or discharge operation starting time for the suction and discharge mechanism and the fluid movement starting time for column tips, the offset of suction or discharge operation quantity and the suction or discharge quantity of the fluid for the column tip after achieving the operation quantity, and the details of the reaction of the packing with substances contained in the subject fluid, while considering the suction or discharge parameter and the difference in time between the suction or discharge operation starting time and the fluid movement starting time for column tips, the offset of suction or discharge operation quantity and the suction or discharge quantity of the fluid for the column tip after achieving the operation quantity, and the details of the reaction of the packing with substances contained in the subject fluid.

18. The optimum parameter generating program according to claim 17, wherein the packing is enclosed in the tip-shaped vessel using at least one filter provided in a manner to partition the tip-shaped vessel, the structural requirement data include a plurality of items relating to the structure of the member or the tip-shaped vessel to be fitted to the nozzle, the structure of the filter or the morphology or nature of the packing enclosed, and the processing requirement data include a plurality of items relating to the processing contents including each housing position, nature or quantity of one or more types of the subject fluids subjected to the suction or discharge of the column tips.

* * * * *